US011166715B2

(12) United States Patent
Courtwright et al.

(10) Patent No.: US 11,166,715 B2
(45) Date of Patent: Nov. 9, 2021

(54) ACTUATOR SUPPORT STRUCTURE FOR SURGICAL STAPLER

(71) Applicant: ETHICON LLC, Guaynabo, PR (US)

(72) Inventors: Nicholas D. Courtwright, Villa Hills, KY (US); Barry Thomas Jamison, Fairfield, OH (US); Michael S. Cropper, Edgewood, KY (US); Bradley A. Arnold, Mason, OH (US)

(73) Assignee: Cilag GmbH International, Zug (CH)

( * ) Notice: Subject to any disclaimer, the term of this patent is extended or adjusted under 35 U.S.C. 154(b) by 149 days.

(21) Appl. No.: 16/410,006

(22) Filed: May 13, 2019

(65) Prior Publication Data
US 2020/0360015 A1    Nov. 19, 2020

(51) Int. Cl.
*A61B 17/068* (2006.01)
*A61B 17/115* (2006.01)
(Continued)

(52) U.S. Cl.
CPC .......... *A61B 17/068* (2013.01); *A61B 17/115* (2013.01); *A61B 17/105* (2013.01);
(Continued)

(58) Field of Classification Search
CPC ............ A61B 17/068; A61B 17/07207; A61B 17/105; A61B 17/115; A61B 2017/00367;
(Continued)

(56) References Cited

U.S. PATENT DOCUMENTS 5,636,779 A * 6/1997 Palmer ................. A61B 17/072
227/175.2
5,988,479 A * 11/1999 Palmer ............. A61B 17/07207
227/175.4
(Continued)

FOREIGN PATENT DOCUMENTS

CN    202 942 167 U    5/2013
WO    WO 2015/065482 A1    5/2015

OTHER PUBLICATIONS

U.S. Appl. No. 16/409,957, entitled "Actuator Retainer for Surgical Stapler," filed May 13, 2019.
(Continued)

*Primary Examiner* — Andrew M Tecco
*Assistant Examiner* — Nicholas E Igbokwe
(74) *Attorney, Agent, or Firm* — Frost Brown Todd LLC

(57) ABSTRACT

A surgical stapler includes first and second elongate members, a clamp member, and a firing assembly. The second elongate member is configured to receive a staple cartridge. The clamp member is operable to releasably clamp the first elongate member against the second elongate member. The firing assembly is translatable to fire the staple cartridge. The firing assembly includes a slider and an actuator configured to be selectively actuated by a user. The slider includes inner and outer engagement features. The actuator includes inner and outer engagement features. The inner engagement feature of the actuator is configured to engage with the inner engagement feature of the slider at a first interface when the actuator moves relative to the slider. The outer engagement
(Continued)

feature of the actuator is configured to engage the outer engagement feature of the slider at a second interface when the actuator moves relative to the slider.

20 Claims, 17 Drawing Sheets

(51) Int. Cl.
*A61B 17/10* (2006.01)
*A61B 17/00* (2006.01)
*A61B 17/072* (2006.01)

(52) U.S. Cl.
CPC .......... *A61B 2017/0046* (2013.01); *A61B 2017/0725* (2013.01); *A61B 2017/07257* (2013.01); *A61B 2017/07271* (2013.01); *A61B 2017/07285* (2013.01)

(58) Field of Classification Search
CPC .... A61B 2017/0725; A61B 2017/0042; A61B 2017/00429; A61B 2017/0046; A61B 2017/00477; A61B 2017/07257; A61B 2017/07285; A61B 2017/07271
See application file for complete search history.

(56) References Cited

U.S. PATENT DOCUMENTS

| | | | |
|---|---|---|---|
| 7,905,381 | B2 | 3/2011 | Baxter, III et al. |
| 7,954,686 | B2 | 6/2011 | Baxter, III et al. |
| 8,348,129 | B2 | 1/2013 | Bedi et al. |
| 8,789,740 | B2 | 7/2014 | Baxter, III et al. |
| 2010/0072253 | A1* | 3/2010 | Baxter, III ....... A61B 17/07207 227/176.1 |
| 2010/0076429 | A1* | 3/2010 | Heinrich .............. A61B 17/115 606/49 |
| 2011/0068145 | A1* | 3/2011 | Bedi .................. A61B 17/0644 227/176.1 |
| 2011/0084115 | A1* | 4/2011 | Bedi .................. A61B 17/0686 227/179.1 |
| 2019/0239881 | A1 | 8/2019 | Laurent et al. |
| 2019/0239882 | A1 | 8/2019 | McLain et al. |
| 2019/0239883 | A1 | 8/2019 | Baxter et al. |
| 2019/0239884 | A1 | 8/2019 | Baxter et al. |
| 2019/0239885 | A1 | 8/2019 | Stokes et al. |
| 2019/0239886 | A1 | 8/2019 | Jones et al. |
| 2020/0046350 | A1 | 2/2020 | Deck et al. |

OTHER PUBLICATIONS

European Search Report and Written Opinion dated Dec. 14, 2020 for Application No. EP 20174021.4, 10 pgs.
International Search Report and Written Opinion dated Aug. 24, 2020 for Application No. PCT/IB2020/054251, 13 pgs.

* cited by examiner

ACTUATOR SUPPORT STRUCTURE FOR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
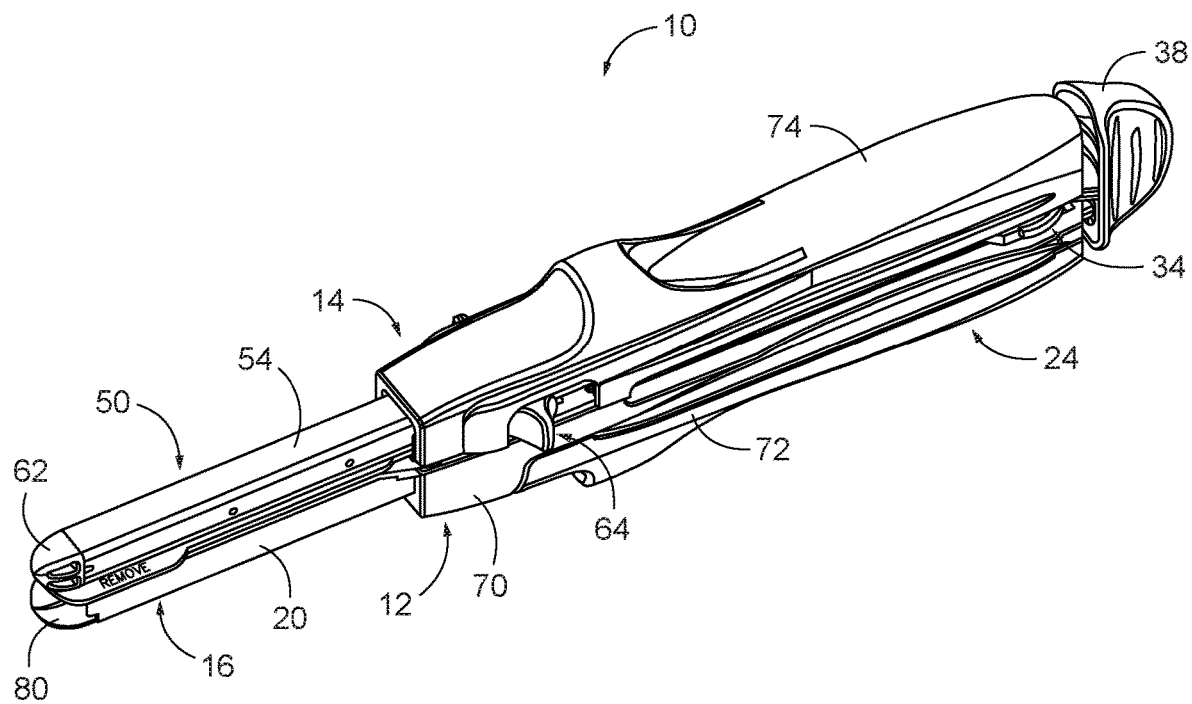
FIG. 1 depicts a distal perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
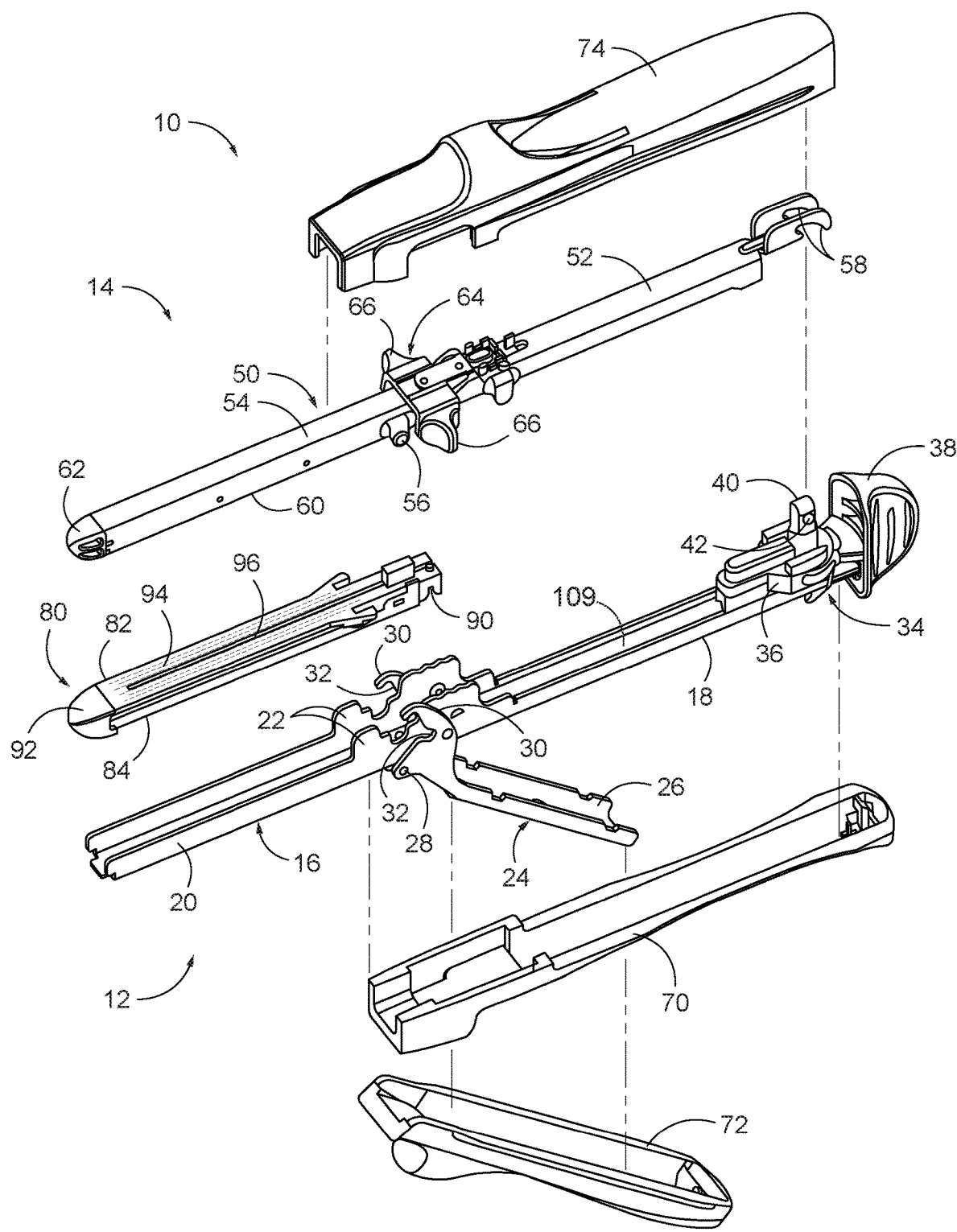
FIG. 2 depicts an exploded perspective view of the linear surgical stapler of FIG. 1.

FIGS. 1 and 2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween. Cartridge half (12) includes a frame (16). Frame (16) is shown as being generally U-shaped to form an elongate channel. Frame (16) includes a proximal frame portion (18), a distal frame portion (20), and a pair of upright side flanges (22) arranged medially therebetween. Proximal frame portion (18) slidably retains a portion of a firing assembly (34). Distal jaw portion (20) supports a staple cartridge (80) (or "reload").

Cartridge half (12) further includes a clamp lever (24) pivotably coupled to an underside of frame (16) in approximate alignment with side flanges (22). Clamp lever (24) includes an elongate lever arm (26) having a free proximal end and a distal end that is pivotably coupled to frame (16) with a pivot pin (28). A pair of opposed jaws (30) extends distally from the distal end of lever arm (26) alongside flanges (22) of frame (16). Each jaw (30) includes a respective elongate slot (32) having a closed proximal end and an open distal end, and which defines upper and lower camming surfaces configured to engage a respective latch projection (56) of anvil half (14). As described below, clamp lever (24) is operable to pivot relative to frame (16) between open and closed positions to releasably clamp anvil half (14) against cartridge half (12) and thereby capture tissue layers therebetween.

As shown best in FIG. 2, firing assembly (34) of cartridge half (12) includes a slider (36), shown schematically, slidably retained within proximal frame portion (18) of frame (16), an actuator (38) (or "firing knob") movably coupled with slider (36), and an elongate actuating beam (not shown) extending distally from slider (36) and configured to couple with a sled (100) (shown in FIG. 3) housed within staple cartridge (80). Actuator (38) of the present example is configured to pivot about the proximal end of cartridge half (12) to provide for "dual-sided firing" of stapler (10). Specifically, actuator (38) may be positioned along either lateral side of cartridge half (12) to perform a distal firing stroke, such that stapler (10) may be conveniently fired in a variety of orientations during a surgical procedure.

Figure 5A:
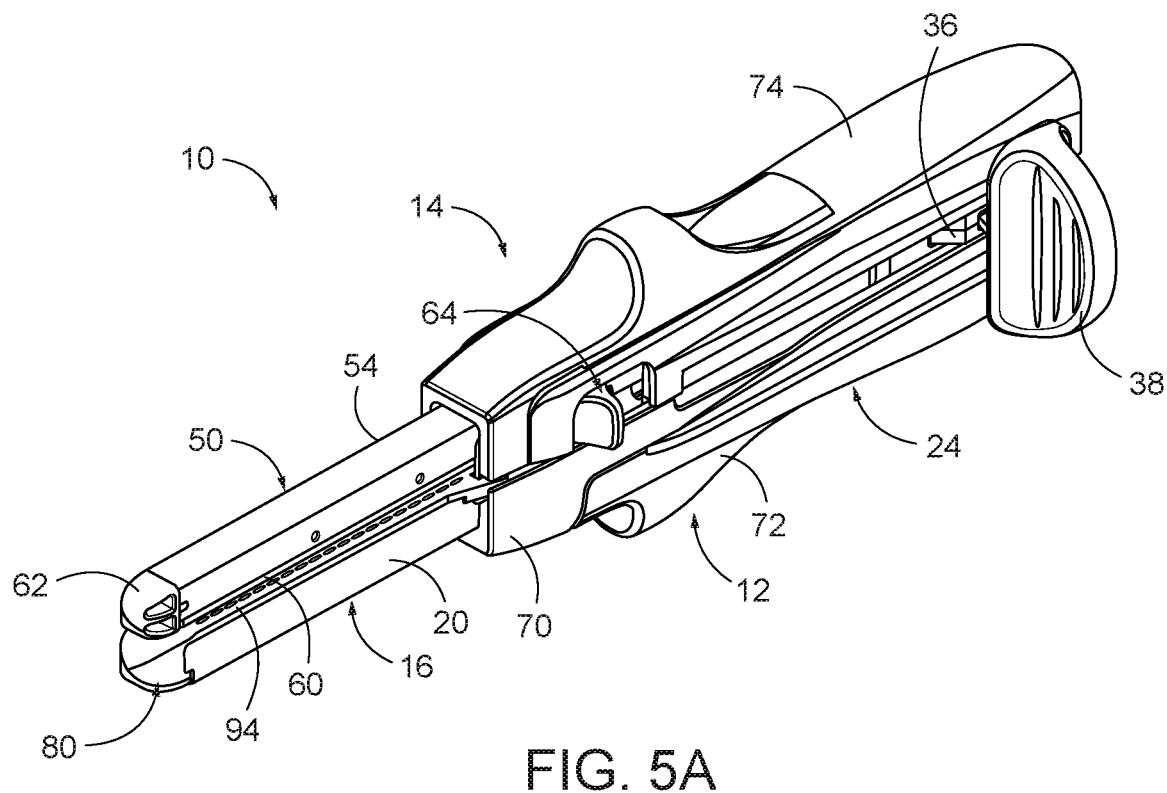
FIG. 5A depicts a distal perspective view of the linear surgical stapler of FIG. 1, showing an actuator of the stapler in a proximal, pre-fired position.
Figure 5B:
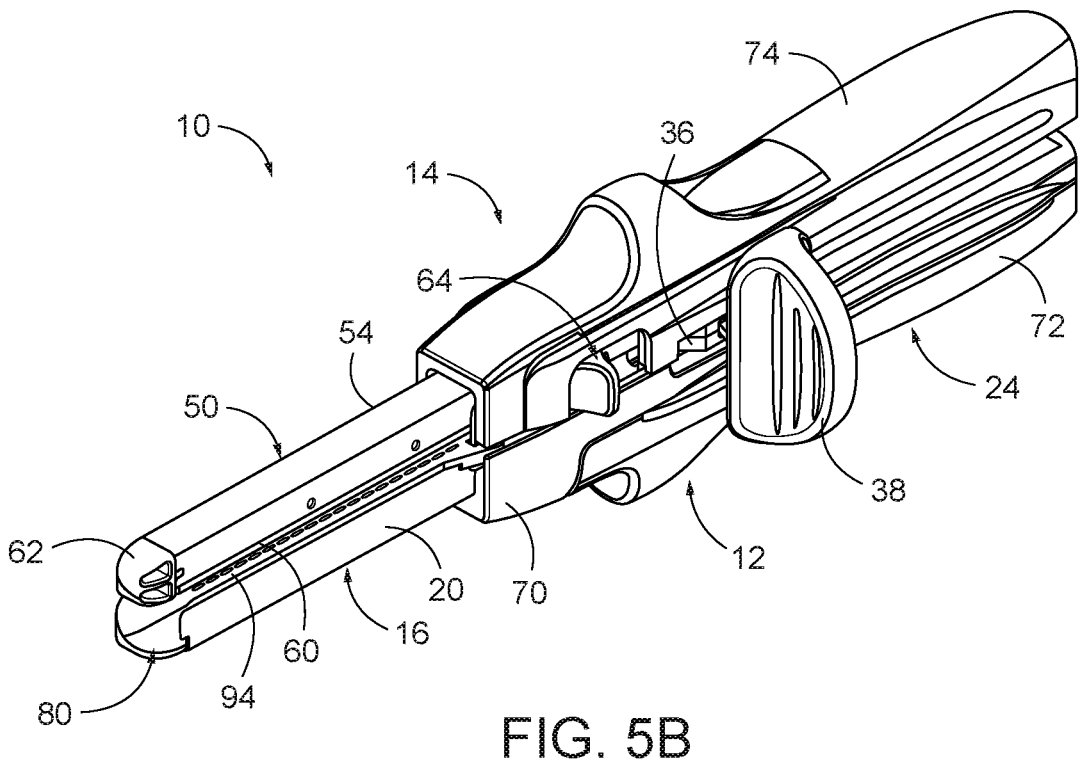
FIG. 5B depicts a distal perspective view of the linear surgical stapler of FIG. 1, showing the actuator in a distal, fired position.

Slider (36) is configured to be translatably driven within proximal frame portion (18) by actuator (38) between a proximal home position shown in FIGS. 2 and 5A, and a distal fired position shown in FIG. 5B. In the proximal home position, slider (36) abuts a post (40) fixed at a proximal end of frame (16). A free end of post (40) supports a laterally extending pivot pin (42). As described below, actuator (38) may be driven distally when stapler halves (12, 14) are fully coupled together and clamp lever (24) is closed. Distal advancement of actuator (38) along either lateral side of stapler (10) drives slider (36) and the elongate actuating beam distally, which in turn drives sled (100) distally through staple cartridge (80). As described below, distal translation of sled (100) through staple cartridge (80) provides for simultaneous stapling and cutting of tissue clamped between stapler halves (12, 14).

As shown best in FIGS. 1 and 2, anvil half (14) of linear surgical stapler (10) includes an elongate anvil channel (50) having a proximal frame portion (52) and a distal jaw portion (54). Anvil channel (50) further includes a latch feature in the form of a pair of projections (56) that extend transversely from a medial portion of anvil channel (50) in a direction toward cartridge half (12). Each latch projection (56) may include a circular rotating cap configured to be captured within slot (32) of a respective clamp lever jaw (30) when anvil half (14) is coupled with cartridge half (12) and clamp lever (24) is pivoted from the open position to the closed position, as described below. A pair of hooks (58) extend proximally from a proximal end of frame portion (52) and are configured to releasably capture opposed lateral ends of proximal pivot pin (42) of cartridge half (12). Distal jaw portion (54) supports an anvil surface in the form of an anvil plate (60) having a plurality of staple forming pockets (not shown), and additionally supports a distal tip member (62). In other versions of stapler (10), the anvil surface may be formed integrally with or otherwise be rigidly connected to distal jaw portion (54) of anvil channel (50).

Anvil half (14) of the present example further includes a staple height adjustment mechanism (64) mounted to a medial portion of anvil channel (50). Staple height adjustment mechanism (64) is operatively coupled with anvil plate (60), for example, via one or more camming features (not shown), and includes a pair of user-engageable projections (66). Longitudinal adjustment of projections (66) between a plurality of predetermined positions causes anvil plate (60) to move transversely relative to distal jaw portion (54) of anvil channel (50). This enables adjustment of a transverse gap distance between anvil plate (60) and a deck (94) of staple cartridge (80) that defines the height of staples being formed. A larger gap distance, and thus a greater staple height, may be set when stapling tissues of greater thicknesses. Conversely, a smaller gap distance, and thus a smaller staple height, may be set when stapling tissues of lesser thicknesses. It will be appreciated that staple height adjustment mechanism (64) may be omitted in some versions, in which case the anvil surface may be fixed relative to anvil channel (50). For instance, the anvil surface may be formed integrally with or otherwise fixedly secured to distal jaw portion (54).

As shown in FIGS. 1 and 2, linear surgical stapler (10) further includes a plurality of shrouds (70, 72, 74) that cover select portions of stapler (10) and promote effective grip and manipulation of stapler (10) by an operator during use. In the present example, cartridge half (12) includes shroud (70) that covers an outwardly facing side of proximal frame portion (18) of frame (16). Cartridge half (12) further includes shroud (72) that covers an outwardly facing side of clamp lever (24) and is configured to pivot with clamp lever (24) relative to frame (16) and shroud (70). Anvil half (14) includes shroud (74) that covers an outwardly facing side of proximal frame portion (52) of anvil channel (50), including proximal hooks (58). Each shroud (70, 72, 74) may be coupled with its respective components of stapler (10) by any suitable means apparent to those of ordinary skill in the art. Additionally, each shroud (70, 72, 74) may be formed of one or more materials and be provided with texturing suitable to promote effective gripping of the shroud (70, 72, 74) by an operator to enable safe and efficient use of stapler (10) during a surgical procedure.

Figure 3:
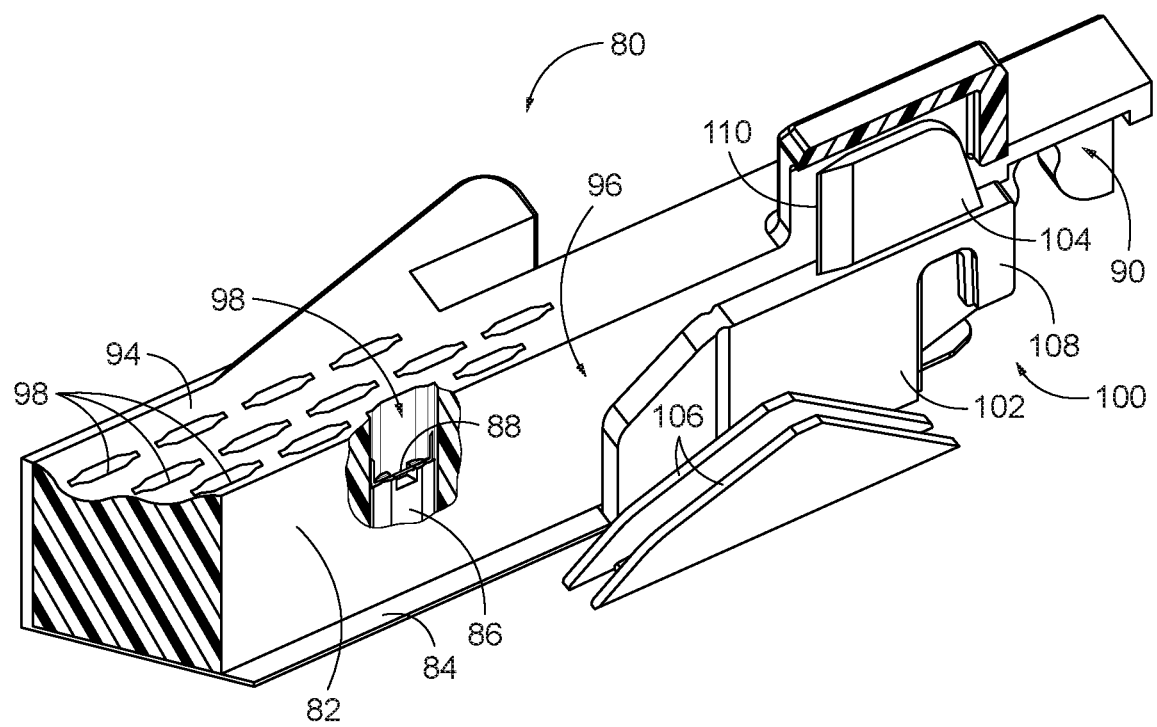
FIG. 3 depicts a cross-sectional perspective view of a staple cartridge assembly of the linear surgical stapler of FIG. 1.

As shown in FIGS. 2 and 3, staple cartridge (80) of the present example is an assembly that comprises a cartridge body (82), a pan (84) that covers an open lower side of cartridge body (82), and a plurality of staple drivers (86) housed within cartridge body (82) and each being configured to drive a respective staple (88). Cartridge body (82) includes a proximal end having engagement features (90) configured to releasably engage corresponding engagement features (not shown) of distal jaw portion (20) of frame (16), and a distal end defining a tapered nose (92). An upper side of cartridge body (82) defines a generally planar deck (94) through which a longitudinal slot (96) and a plurality of staple cavities (98) open. Each staple cavity (98) houses a respective staple driver (86) and staple (88). As shown in FIG. 3, an interior of cartridge body (82) slidably houses sled (100) that comprises a sled body (102) and knife member (104). Lateral sides of sled body (102) support a plurality of cam ramps (106) that taper distally. A proximal end of sled body (102) includes a downwardly extending tab (108) configured to lockingly engage a distal end of the elongate actuating beam (not shown) of firing assembly (34) when staple cartridge (80) is mounted to cartridge half (12) of stapler (10). Knife member (104) extends upwardly from an upper side of sled body (102) and presents a distally facing cutting edge (110) configured to cut tissue.

Sled (100) is configured to translate distally through cartridge body (82) in response to distal actuation of firing assembly (34), such that knife member (104) translates distally through longitudinal slot (96) to cut tissue clamped between stapler halves (12, 14). Simultaneously, cam ramps (106) translate distally through respective interior slots (not shown) of cartridge body (82) to actuate staple drivers (86) and staples (88) upwardly through staple cavities (98) so that free ends of staples (88) pierce through the clamped tissue and deform against staple forming pockets of anvil plate (60). In this manner, distal actuation of firing assembly (34) provides for simultaneous severing and stapling of tissue clamped between the distal end effector portions of stapler halves (12, 14).

Linear surgical stapler (10) and staple cartridge (80) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and/or U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Surgical Stapler

Figure 4A:
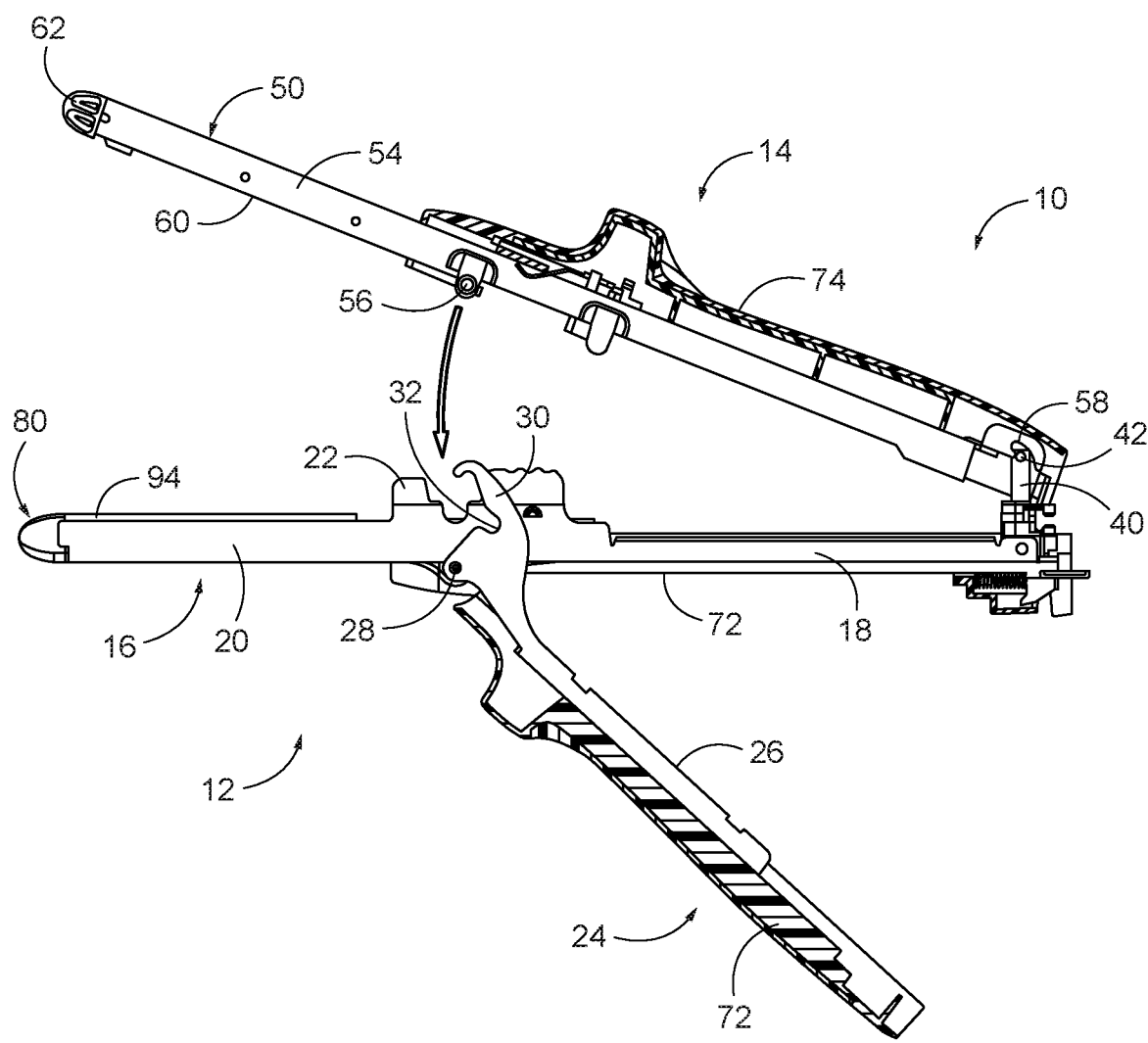
FIG. 4A depicts a cross-sectional side view of the linear surgical stapler of FIG. 1, showing the stapler halves coupled together at their proximal ends with the clamp lever in an open position.
Figure 4B:
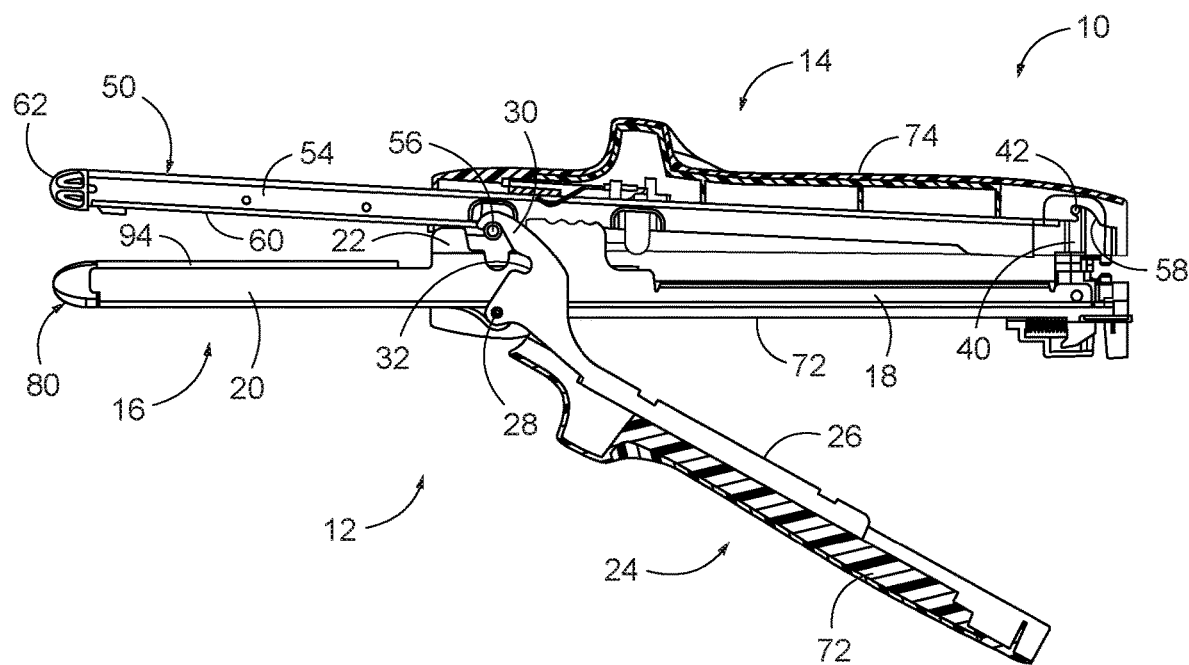
FIG. 4B depicts a cross-sectional side view of the linear surgical stapler of FIG. 1, showing the stapler halves coupled together with the clamp lever in a partially closed position.
Figure 4C:
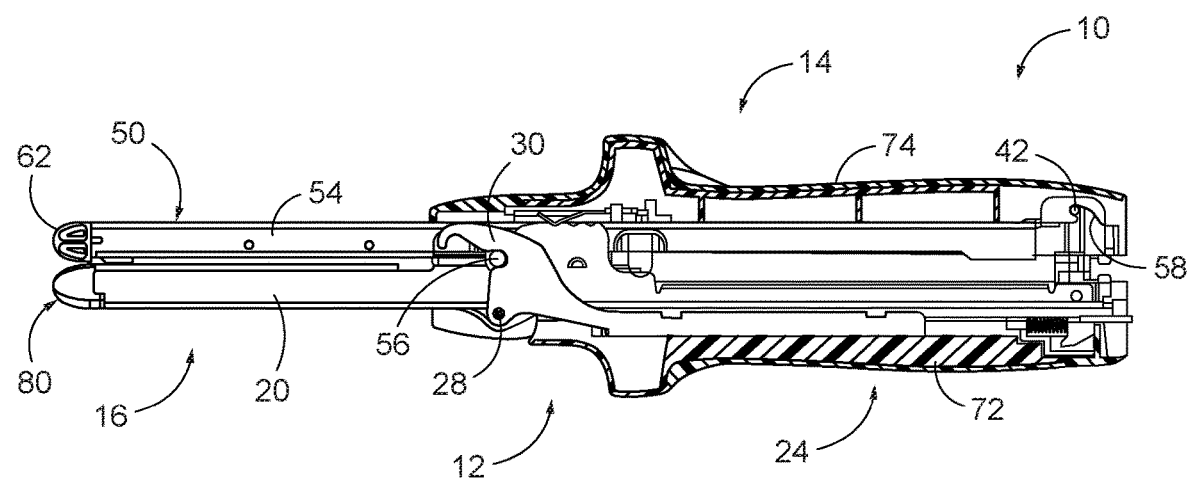
FIG. 4C depicts a cross-sectional side view of the linear surgical stapler of FIG. 1, showing the stapler halves coupled together with the clamp lever in a fully closed position.

FIGS. 4A-4C show exemplary coupling of stapler halves (12, 14) during a surgical procedure. As shown in FIG. 4A, the proximal end of anvil half (14) is aligned with the proximal end of cartridge half (12) such that proximal pivot pin (42) of cartridge half (12) is received by proximal hooks (58) of anvil half (14). With clamp lever (24) in the open position, anvil half (14) is then pivoted toward cartridge half (12), about proximal pivot pin (42), to direct latch projections of anvil half (14) into slots (32) of clamp lever jaws (30). Once latch projections (56) are received by clamp lever jaws (30), clamp lever (24) is pivoted toward the partially closed position shown in FIG. 4B. In this partially closed position of clamp lever (24), anvil half (14) is partially clamped with cartridge half (12) such that stapler (10) may now be held with a single hand without halves (12, 14) undesirably separating from one another. Additionally, in this state, the distal portions of stapler halves (12, 14) remain spaced apart from one another to permit positioning of tissue between the distal portions. It will be appreciated that tissue may be positioned between the distal portions of stapler halves (12, 14) before or upon achieving this partially clamped state.

As shown in FIG. 4C, clamp lever (24) is then pivoted further toward its fully closed position such that the camming surfaces of clamp lever jaws (30) draw latch projections of anvil half (14) proximally against the closed proximal ends of slots (32) of clamp lever jaws (30), thereby fully clamping stapler halves (12, 14) together with tissue positioned securely therebetween. Once halves (12, 14) of stapler (10) are in a fully clamped state, actuator (38) may be manipulated to fire staple cartridge (80). In particular, as shown in FIGS. 5A and 5B, actuator (38) is pivoted about the proximal end of stapler (10) to overlie one of the lateral sides of stapler (10). Actuator (38) is then driven distally to actuate firing assembly (34) in the manner described above and thereby simultaneously sever and staple the clamped tissue. Upon completing a distal firing stroke, actuator (38) may be returned to its proximal home position shown in FIG. 2, and clamp lever (24) may then be opened to separate stapler halves (12, 14) from one another and release the stapled and severed tissue.

C. Exemplary Firing Assembly

Figure 6:
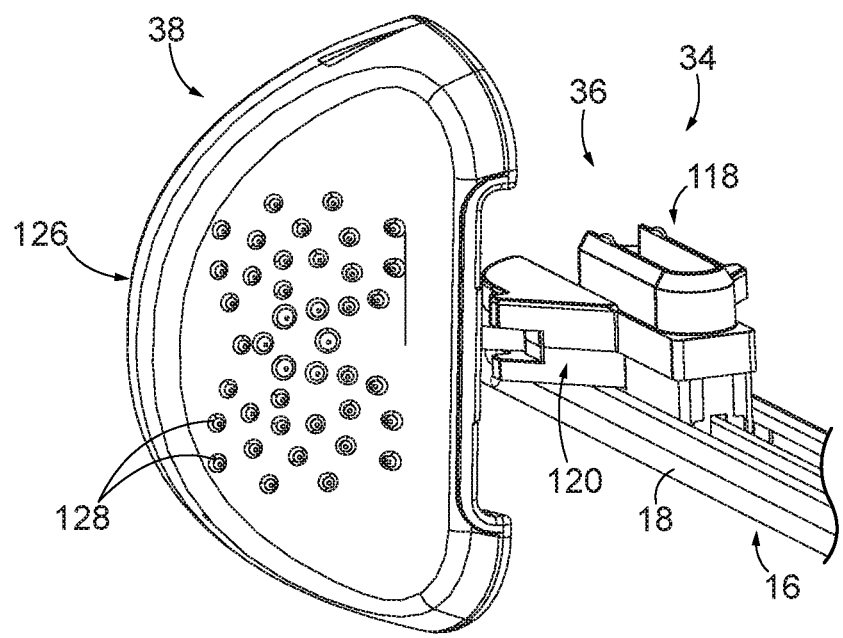
FIG. 6 depicts a distal perspective view of the firing assembly of the linear surgical stapler of FIG. 1.
Figure 7:
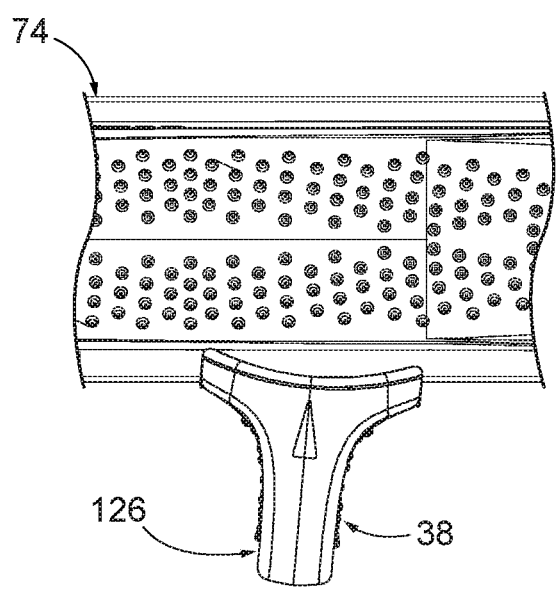
FIG. 7 depicts a top view of the actuator angled relative to a shroud of the linear surgical stapler of FIG. 1.

FIGS. 6-10 show details of firing assembly (34) of linear surgical stapler (10) of FIG. 2. As previously described with reference to FIGS. 5A-5B, firing assembly (34) is translatable from a first longitudinal position to a second longitudinal position to fire staple cartridge (80) when first elongate member (shown as anvil half (14)) is clamped against second elongate member (shown as cartridge half (12)). FIG. 6 shows a distal perspective view of firing assembly (34) of linear surgical stapler (10) of FIG. 1. As previously described, firing assembly (34) includes slider (36) and actuator (38). FIG. 7 shows a top view of actuator (38)

angled relative to a shroud (74) of linear surgical stapler (10) of FIG. 1, which may occur when an off-center load is applied to actuator (38).

Figure 8:
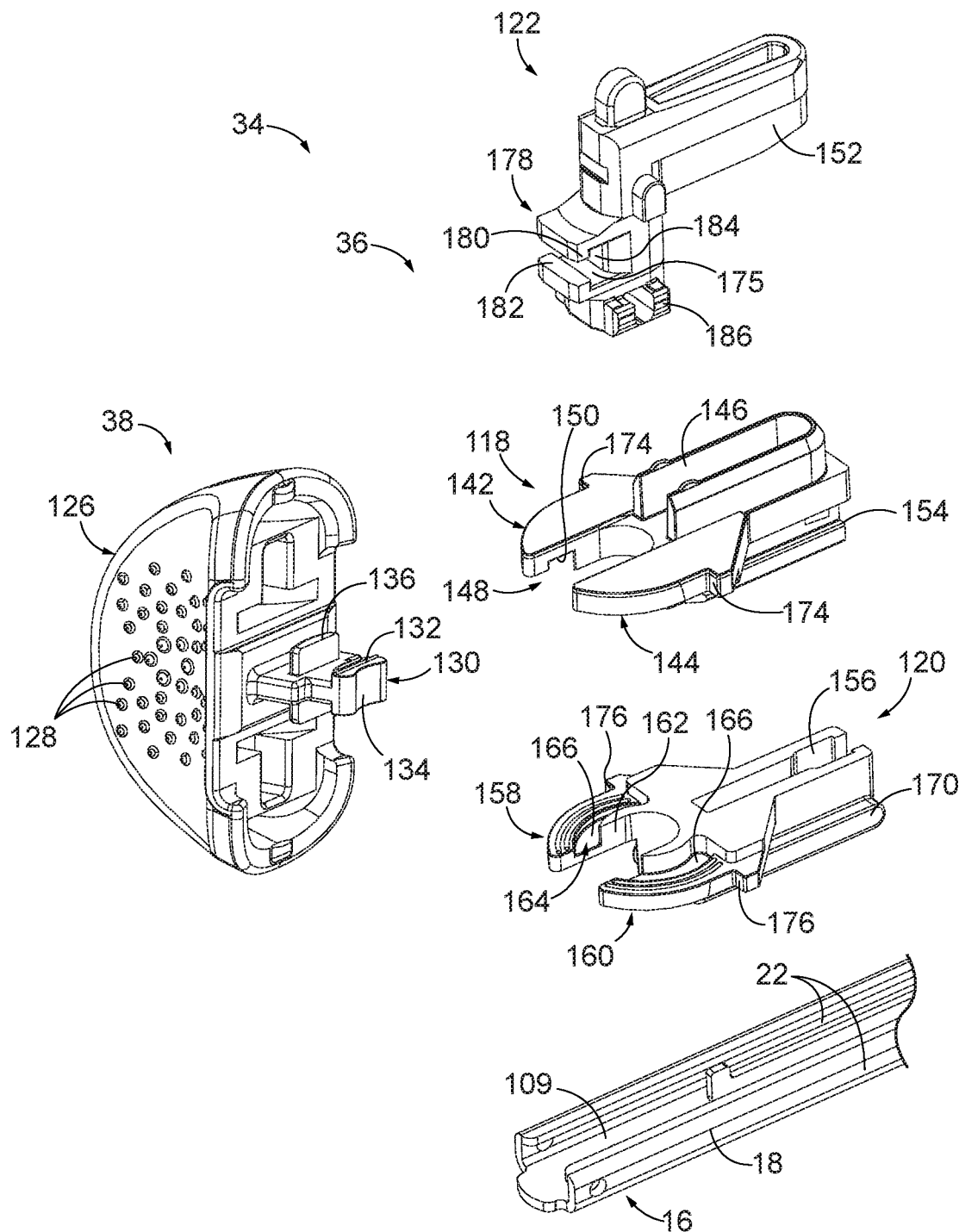
FIG. 8 depicts an exploded proximal perspective view of the firing assembly of FIG. 6, where the firing assembly includes the actuator, an upper body portion, a lower body portion, and a central body portion that are slidable along a frame of FIG. 2.
Figure 9:
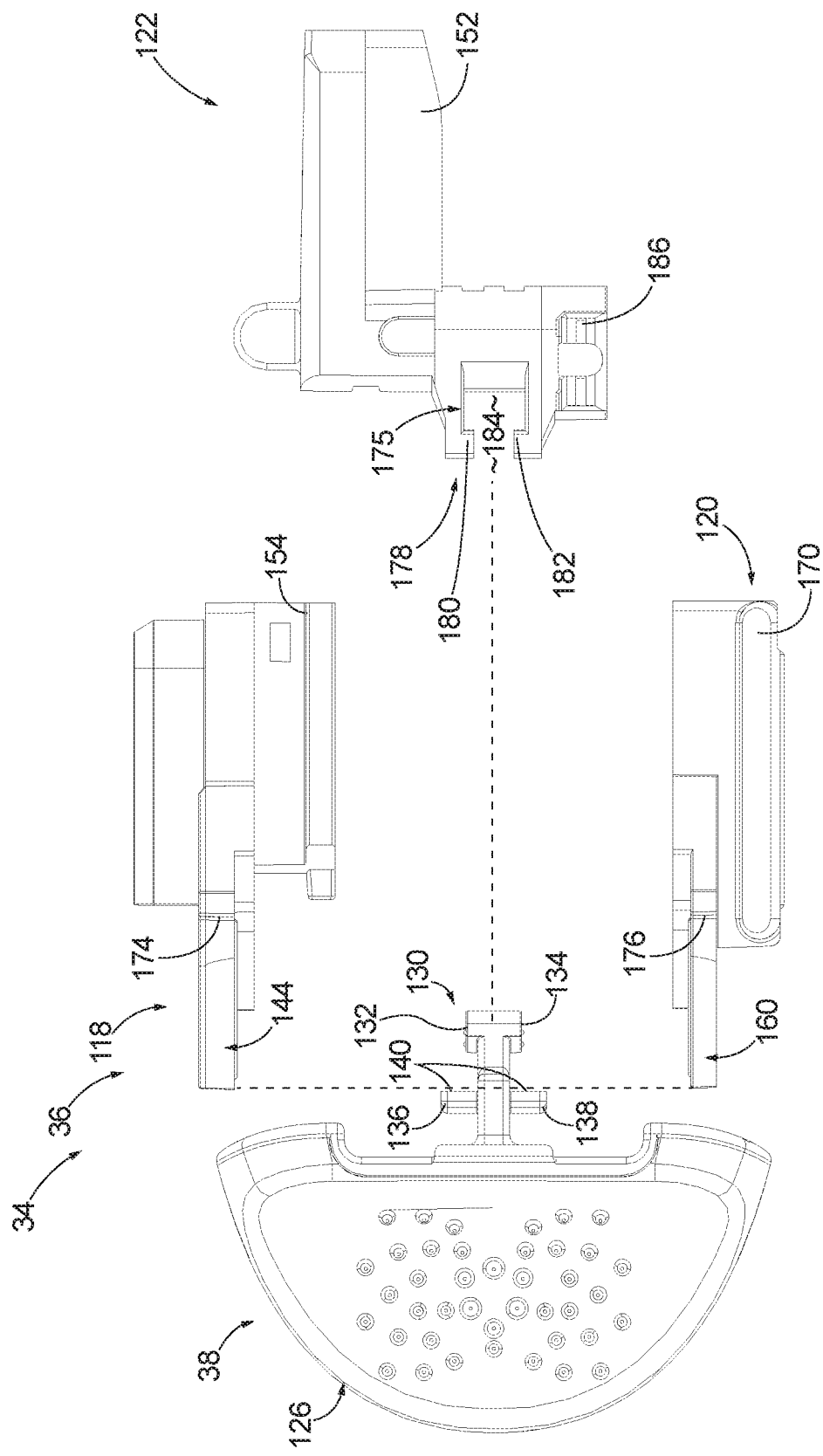
FIG. 9 depicts an exploded side elevational view of the firing assembly and the frame of FIG. 6, where the actuator, the upper body portion, the lower body portion, and the central body portion each include inner engagement features.

As will be described in greater detail below with reference to the following figures, slider (36) includes a first body portion (shown as upper body portion (118)), a second body portion (shown as lower body portion (120)), and a third body portion (shown as central body portion (122)). FIG. 8 shows an exploded proximal perspective view of firing assembly (34) of FIG. 6, where slider (36) is slidably engaged with an elongate channel (109) of proximal frame portion (18) of cartridge half (12) of FIG. 2, such that slider (36) and actuator (38) move longitudinally as a unit along elongate channel (109). FIG. 9 shows an exploded side elevational view of actuator (38), and upper, lower, and central body portions (118, 120, 122) of firing assembly (34) of FIG. 6.

Actuator (38) is described below with reference to FIGS. 6-10. Actuator (38) is configured to transmit force applied by the user to firing assembly (34) to perform a transection of tissue. Actuator (38) includes a body (126), where body (126) may include gripping features (128) for improved gripping by a user. Actuator (38) includes an inner engagement feature (130) that extends away from body (126) of actuator (38). As shown, inner engagement feature (130) includes upper and lower arcuate inner projections (132, 134) that face in opposite directions from one another. Actuator (38) also includes upper and lower outer projections (136, 138) that also face in opposite directions from one another. As shown, upper and lower arcuate inner projections (132, 134) and upper and lower outer projections (136, 138) extend vertically, and parallel, to body (126) of actuator (38). In other words, upper arcuate inner projection (132) and upper outer projection (136) both face vertically upwards, while lower arcuate inner projection (134) and lower outer projection (138) both face vertically downwards. Particularly, upper and lower outer projections (136, 138) have a smooth inner surface (140) that extends vertically without any projections or other features extending therefrom.

Upper and lower body portions (118, 120) are configured to longitudinally slide into central body portion (122) to collectively form slider (36). Upper body portion (118) includes first and second arms (142, 144) that are separated by a longitudinal slot (146) (shown in FIG. 8). First and second arms (142, 144) of upper body portion (118) include an inner engagement feature (148). As shown, inner engagement feature (148) is an upper arcuate inner recess (150) that opens into longitudinal slot (146). Upper arcuate inner recess (150) is configured to securably receive and retain upper arcuate inner projection (132) of inner engagement feature (130) of actuator (38). Longitudinal slot (146) is configured to receive central body portion (122). Particularly, longitudinal slot (146) is configured to accommodate and receive a distal projection (152) of central body portion (122). Upper body portion (118) includes a lower distal projection (154) (shown in FIG. 8) that is configured to be received within a distal slot (156) of lower body portion (120).

Similarly, lower body portion (120) includes first and second arms (158, 160) that are separated by a longitudinal slot (162) (shown in FIG. 8). First and second arms (158, 160) of lower body portion (120) include an inner engagement feature (164) configured to securably receive and retain inner engagement feature (130) of actuator (38). As shown, inner engagement feature (164) is a lower arcuate inner recess (166) that opens into longitudinal slot (162). Upper and lower arcuate inner recesses (150, 166) of upper and lower body portions (118, 120) collectively define a cavity (168) that collectively capture upper and lower arcuate inner projections (132, 134) of inner engagement feature (130) of actuator (38) within cavity (168). Longitudinal slot (162) is configured to receive central body portion (122). As shown in FIG. 8, lower body portion (120) includes lower rails (170). Actuator (38) may be rotated relative to slider (36) until actuator (38) contacts a stop feature (174) of upper body portion (118) and a stop feature (176) of lower body portion (120).

FIGS. 8-9 show central body portion (122) including an inner engagement feature (175). Inner engagement feature (175) may be a C-shaped engagement feature (178), that engages upper and lower arcuate inner projections (132, 134) of inner engagement feature (130) of actuator (38). C-shaped engagement feature (178) includes upper and lower retention features (180, 182) that oppose one another and are shown as being vertically oriented. C-shaped engagement feature (178) forms a cavity (184) that receives upper and lower arcuate inner projections (132, 134) of inner engagement feature (130). Central body portion (122) includes lower rails (186). Lower rails (170) of lower body portion (120) and lower rails (186) of central body portion (122) are configured to slide along elongate channel (109), that forms a track, to vertically guide slider (36) when moved distally.

Figure 10:
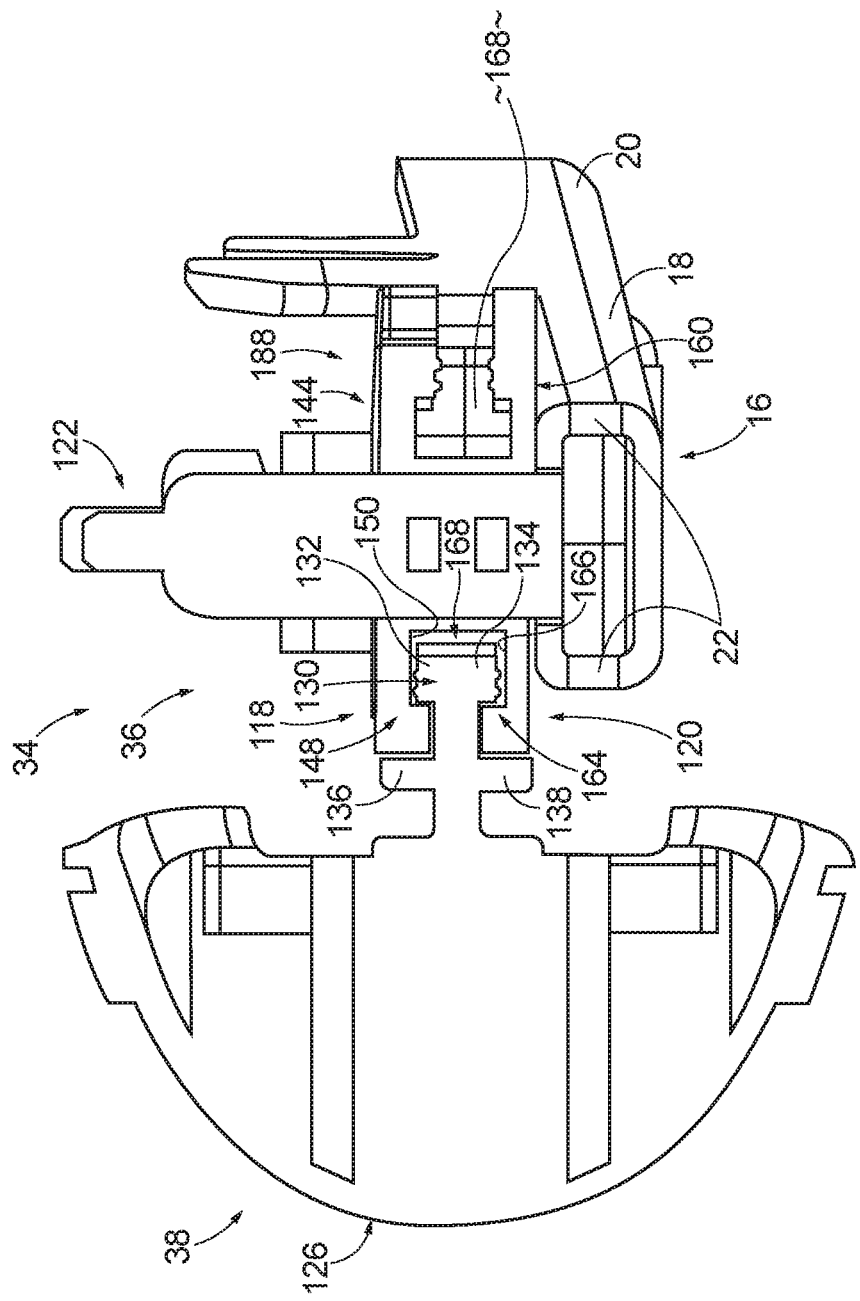
FIG. 10 depicts a proximal cross-sectional perspective view of the linear surgical stapler of FIG. 6, where the inner coupling feature of the first and second body portions engaged with the inner coupling feature of the actuator.

FIG. 10 shows a proximal cross-sectional perspective view of linear surgical stapler (10) of FIG. 6, where a C-shaped engagement feature (188) collectively formed by upper and lower body portions (118, 120) is engaged with upper and lower arcuate inner projections (132, 134) of inner engagement feature (130) of actuator (38). As such, C-shaped engagement feature (178) of central body portion (122) and C-shaped engagement feature (178) collectively formed by upper and lower body portions (118, 120) create cavities (168, 184) that are aligned to provide a track to prevent inner engagement feature (130) of actuator (38) from detaching.

II. Exemplary Linear Surgical Staplers Having Improved Actuator Support

In situations where the user applies an off-centered load to actuator (38) of linear surgical stapler (10), high torsional forces are applied to individual components of firing assembly (34). The high torsional forces may cause deflection of the individual components of firing assembly (34), which may allow the individual components to separate from one another. For example, these individual components may include actuator (38), upper body portion (118), lower body portion (120), and/or central body portion (122). For example, FIG. 7 shows a top view of actuator (38) angled relative to a first shroud of linear surgical stapler (10) of FIG. 1 when an off-center load is applied to actuator (38). Additionally, this deflection may provide an opportunity for actuator (38) to detach from slider (36), which is undesirable. As a result, it may be desirable to strengthen the interface of slider (36) and actuator (38) to prevent, or at least minimize, the deflection of these individual components of firing assembly (34).

As described in greater detail below with reference to FIGS. 11-16B, an exemplary alternative firing system (212) and exemplary linear surgical stapler (310) may limit localized stresses and related deflections on actuator (216, 316) when surgeon-applied, off-center loading creates a torsional load within firing assemblies (212, 312). Firing system (212) and linear surgical stapler (310) enable the individual components of firing assemblies (212, 312) to remain in close proximity to each other and behave as an integrated system rather than individual components during high firing force scenarios. For example, as described below with reference to FIGS. 11-17, the interface of the individual components of firing assembly (34) may be transformed to firing assembly (212) to minimize undesirable deflection of firing assembly (212). Additionally, as described below with reference to FIGS. 18-19, the interface between shrouds (70, 74) and actuator (316) of linear surgical stapler (310) may be transformed to strengthen the interface and minimize undesirable deflection.

A. Exemplary Alternative Firing Assembly for Improved Actuator Support

FIGS. 11-17 show a first exemplary alternative firing assembly (212) for use with a linear surgical stapler, such as linear surgical stapler (10) described above. Firing assembly (212) may be used in place of firing assembly (34) to strengthen firing assembly (212) and minimize undesirable deflection of firing assembly (212). Similar to firing assembly (34), firing assembly (212) is translatable from a first longitudinal position to a second longitudinal position to fire staple cartridge (80) when anvil half (14) is clamped against cartridge half (12).

Figure 11:
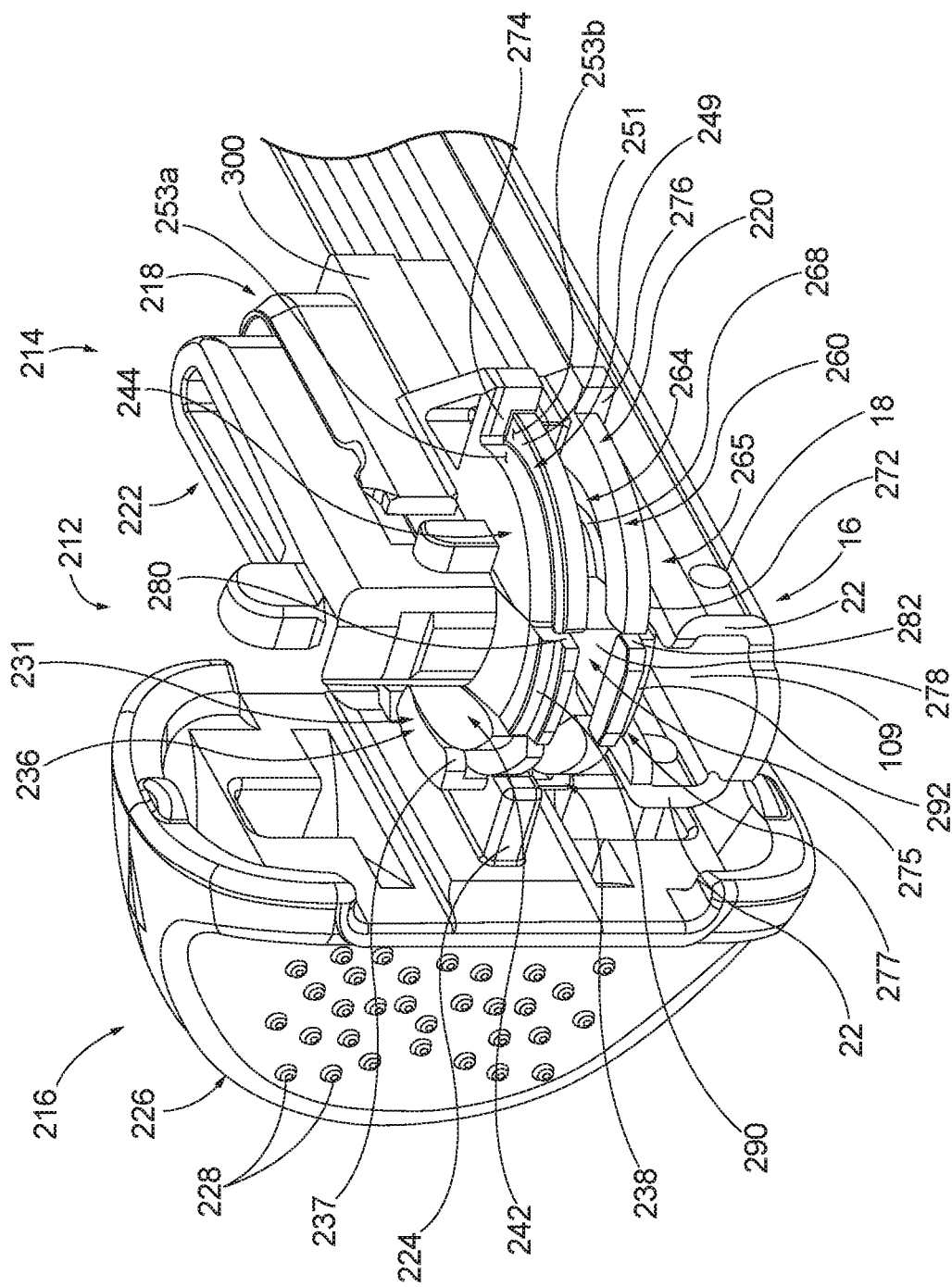
FIG. 11 depicts a perspective view of an exemplary alternative firing assembly of the linear surgical stapler of FIG. 1, where the firing assembly includes an exemplary actuator and an exemplary slider that is slidable along the frame of FIG. 2.

FIG. 11 shows a perspective view of firing assembly (212) as including a slider (214) and an actuator (216), that are similar to slider (36) and actuator (38) described above. Slider (214) includes a first body portion (shown as upper body portion (218)), a second body portion (shown as lower body portion (220)), and a third body portion (shown as central body portion (222)). Upper, lower, and central body portions (218, 220, 222) are similar to upper, lower, and central body portions (118, 120, 122) described above, except as otherwise noted. Upper and lower body portions (218, 220) may be configured to slide longitudinally into central body portion (222) to collectively form slider (214). Upper, lower, and central body portions (218, 220, 222) may be slidable along proximal frame portion (18) of frame (16). Slider (214) is slidably engaged with an elongate channel (109) of proximal frame portion (28) of cartridge half (12) of FIG. 2, such that slider (214) and actuator (216) may move longitudinally as a unit along elongate channel (109) of proximal frame portion (18).

Figure 12:
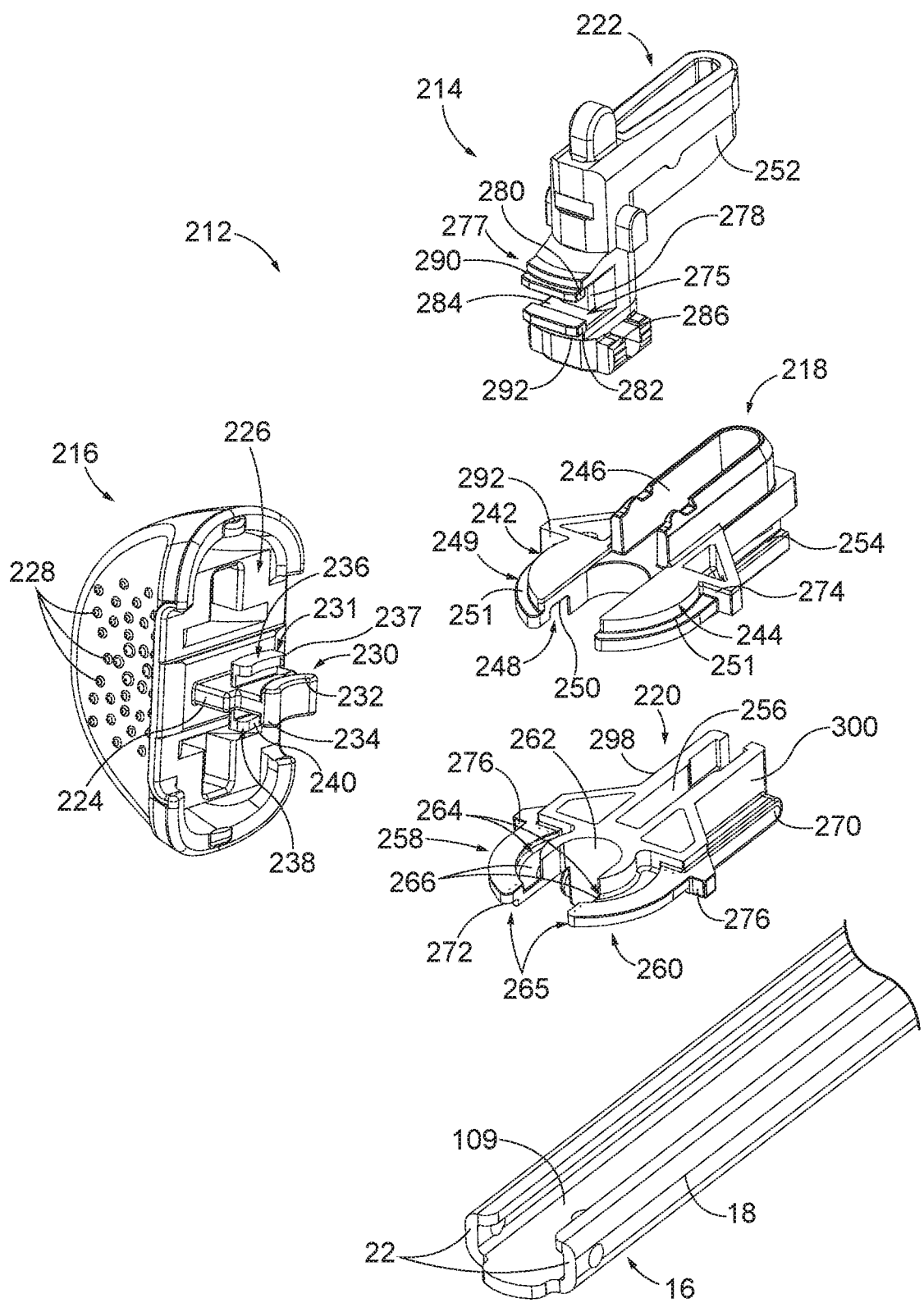
FIG. 12 depicts an exploded perspective view of the firing assembly of FIG. 11, where the firing assembly includes the actuator, an upper body portion, a lower body portion, and a central body portion that are slidable along the frame of FIG. 2.
Figure 13:
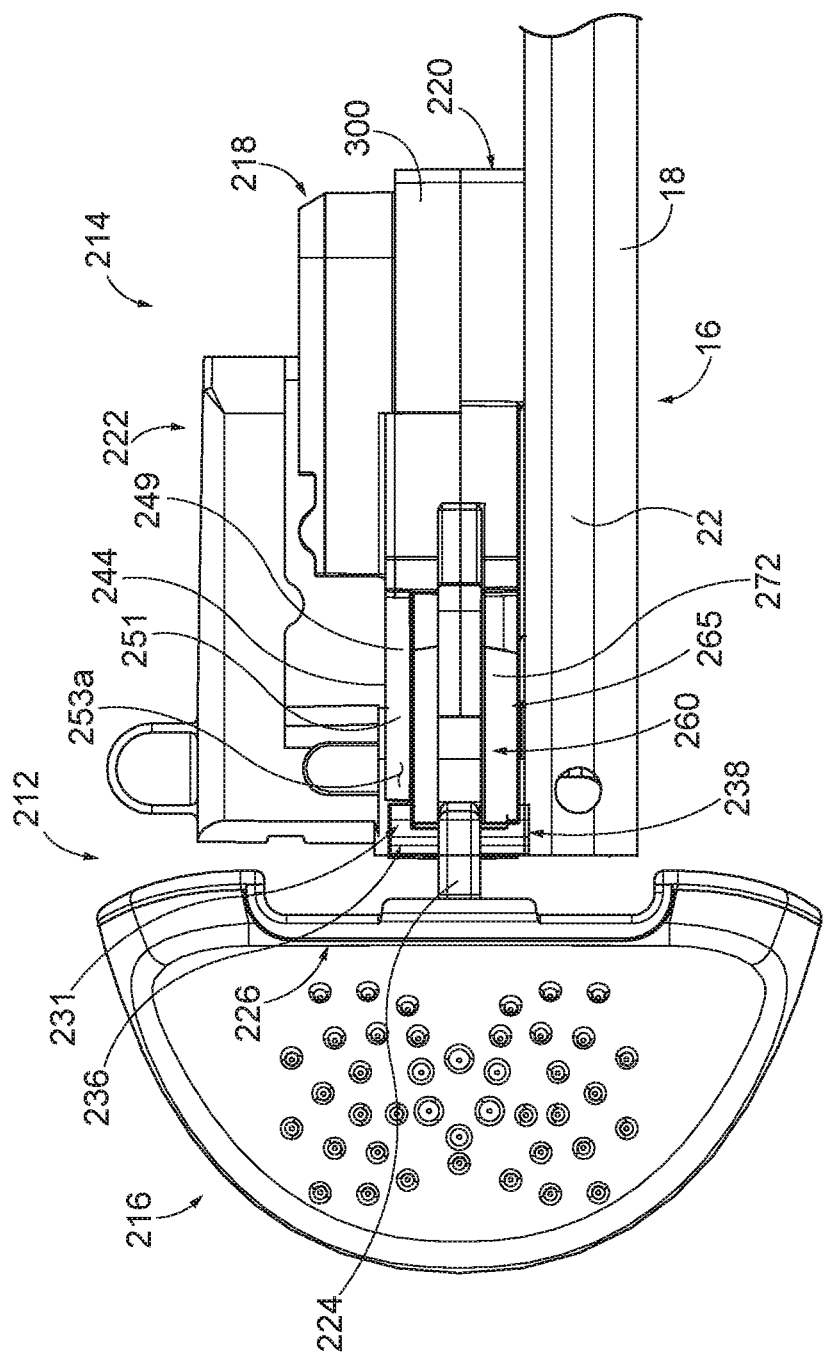
FIG. 13 depicts a side elevational view of the firing assembly of FIG. 11.
Figure 14:
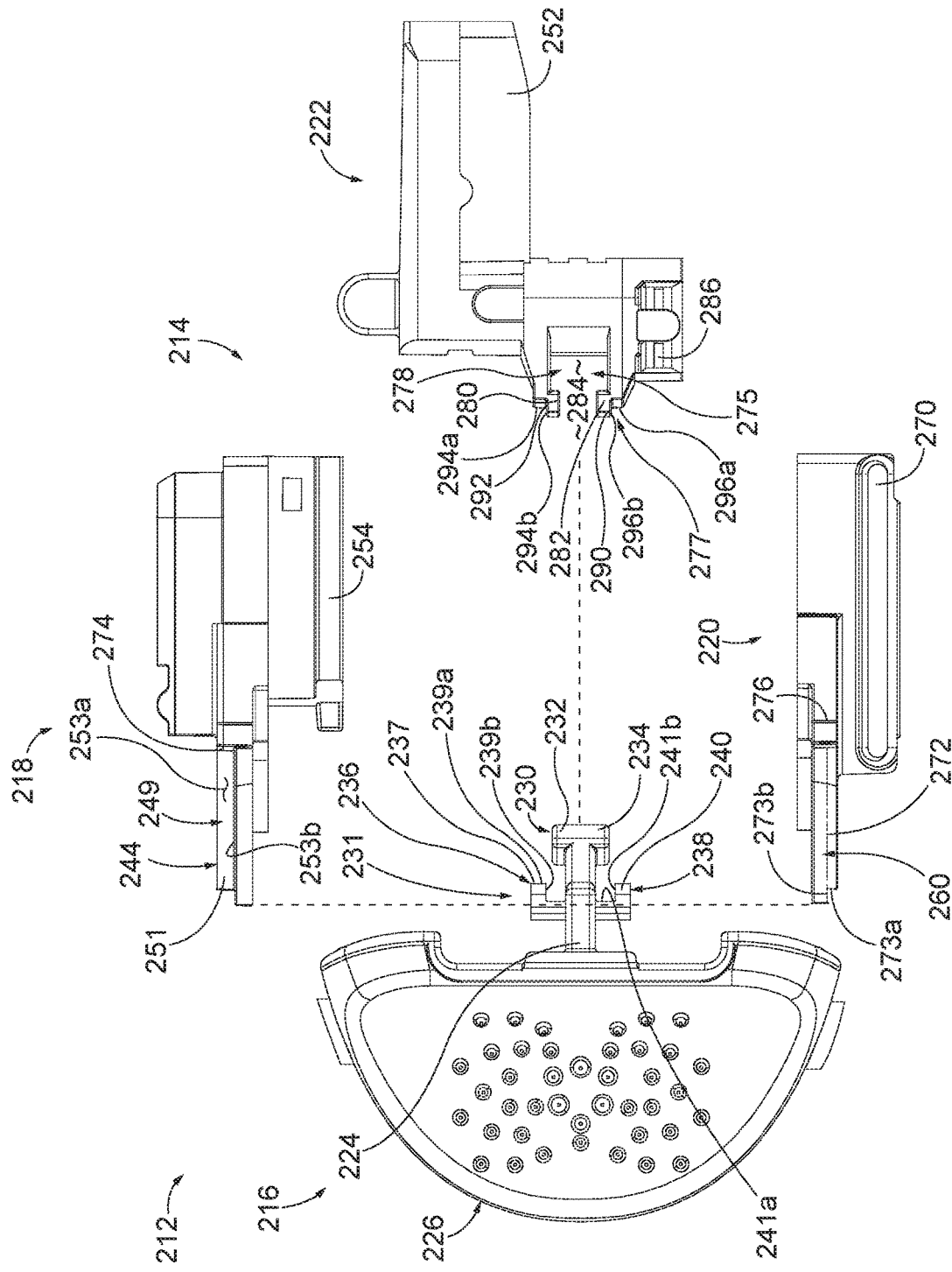
FIG. 14 depicts an exploded side elevational view of the firing assembly of FIG. 11, where the actuator, the upper body portion, the lower body portion, and the central body portion each include inner and outer engagement features.

FIGS. 12-14 describe upper, lower, and central body portions (218, 220, 222) in greater detail. FIG. 12 shows an exploded perspective view of firing assembly of FIG. 11, so that individual features of upper, lower, and central body portions (218, 220, 222) are more easily envisioned. FIG. 13 shows a side elevational view of firing assembly of FIG. 11, showing the coupling of features of upper, lower, and central body portions (218, 220, 222) with actuator (216). FIG. 14 shows an exploded side elevational view of actuator (216) and upper, lower, and central body portions (218, 220, 222) of firing assembly (212) of FIG. 11, where actuator (216) and upper, lower, and central body portions (218, 220, 222) each include features to strengthen firing assembly (212) and minimize undesirable deflection of firing assembly (212) as described below.

1. Exemplary Actuator

Figure 16:
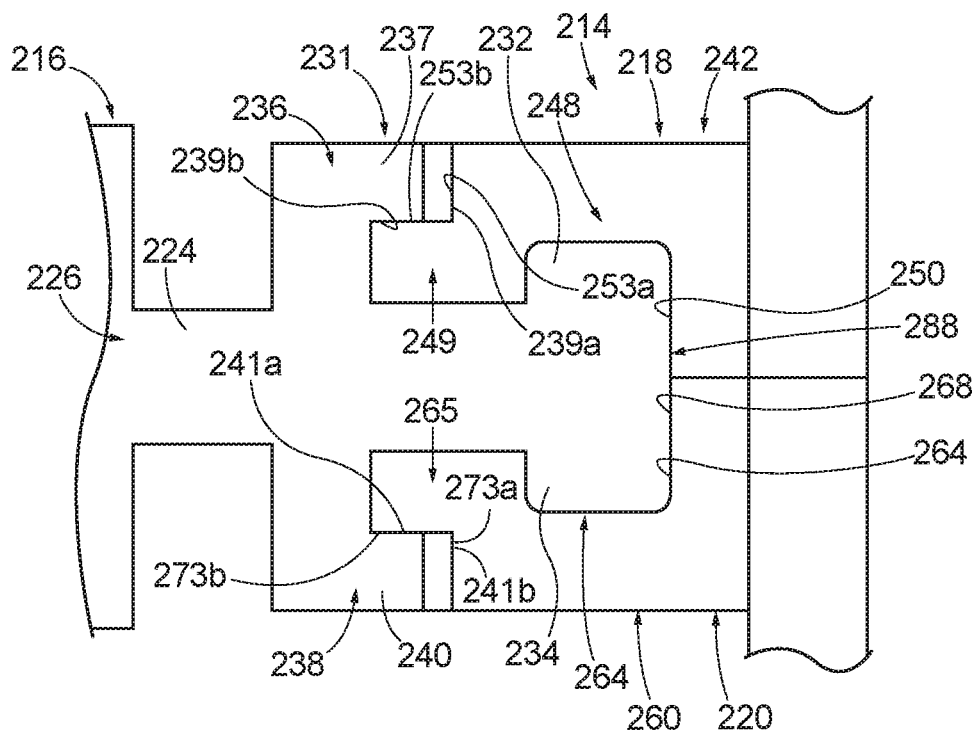
FIG. 16 depicts an enlarged cross-sectional perspective view of an enlarged portion of the firing assembly of FIG. 15.

Actuator (216) is described in greater detail below with reference to FIGS. 11-14A. Similar to actuator (38), actuator (216) is selectively actuated by a user to transmit force applied by the user to firing assembly (212) to perform a transection of tissue. Actuator (216) includes an arm (224) and a body (226). Body (226) may include gripping features (228) for improved gripping by a user. As shown, arm (224) extends perpendicular to body (226) of actuator (216). Arm (224) include inner and outer engagement features (230, 231). Inner engagement feature (230) extends away from body (226) of actuator (216). As shown, inner engagement feature (230) includes upper and lower arcuate inner projections (232, 234) that face in opposite directions from one another. As shown in FIGS. 14 and 16, upper and lower arcuate inner projections (232, 234) extend vertically. Particularly, upper and lower arcuate inner projections (232, 234) extend perpendicular to arm (224) and parallel to body (226).

Unlike actuator (38) described above, actuator (216) includes outer engagement feature (231). Outer engagement feature (231) may include upper and lower projections configured to strengthen the interface between slider (214) and actuator (216). Particularly, outer engagement feature (231) is shown as including upper and lower L-shaped arcuate outer projections (236, 238). However, it is also envisioned that outer engagement feature (231) may have a variety of suitable shapes and sizes. Upper and lower L-shaped arcuate outer projections (236, 238) extend in opposite directions away from arm (224). Upper L-shaped arcuate outer projection (236) includes an upper tip portion (237). As shown in FIGS. 14 and 16, upper tip portion (237) includes a vertical interface surface (239*a*) and a horizontal interface surface (239*b*). Similarly, lower L-shaped arcuate outer projection (238) includes a lower tip portion (240). As shown in FIGS. 14 and 16, lower tip portion (240) includes a vertical interface surface (241*a*) and a horizontal interface surface (241*b*). Upper and lower tip portions (237, 240) of upper and lower L-shaped arcuate outer projections (236, 238) are shown as extending parallel to arm (224) of actuator (216). As shown, a lower half of actuator (216) is a mirror image of upper half of actuator (216).

2. Exemplary Upper Body Portion

Upper body portion (218) includes first and second arms (242, 244) that are separated by a longitudinal slot (246) (shown in FIG. 12). First and second arms (242, 244) of upper body portion (218) include an inner engagement feature (248) and an outer engagement feature (249). As shown, inner engagement feature (248) is an upper arcuate inner recess (250) that opens into longitudinal slot (246) and (downwardly) toward lower body portion (220). Upper arcuate inner recess (250) is configured to securably receive and retain upper arcuate inner projection (232) of inner engagement feature (230) of actuator (216). Longitudinal slot (246) is configured to receive central body portion (222). Particularly, longitudinal slot (246) is configured to accommodate and receive a distal projection (252) of central body portion (222). Upper body portion (218) includes a lower distal projection (254) (shown in FIGS. 12 and 14) that is configured to be received within a distal slot (256) of lower body portion (220).

Unlike upper body portion (118) described above, upper body portion (218) includes outer engagement feature (249), which is shown an upper arcuate outer recess (251). However, it is also envisioned that outer engagement feature (249) may have a variety of suitable shapes and sizes. Upper arcuate outer recess (251) opens upwardly in an opposite direction than upper arcuate inner recess (250). Upper arcuate outer recess (251) includes a vertical interface surface (253*a*) and a horizontal interface surface (253*b*) that are shown as being perpendicular to each other.

3. Exemplary Lower Body Portion

Lower body portion (220) includes first and second arms (258, 260) that are separated by a longitudinal slot (262) (shown in FIG. 12). First and second arms (258, 260) of lower body portion (220) include an inner engagement feature (264) and an outer engagement feature (265). Inner engagement feature (264) is configured to securably receive and retain inner engagement feature (230) of actuator (216). As shown, inner engagement feature (264) is a lower arcuate inner recess (266) that opens into longitudinal slot (262). Upper and lower arcuate inner recesses (250, 266) of upper and lower body portions (218, 220) collectively define a cavity (268) that collectively capture upper and lower arcuate inner projections (232, 234) of inner engagement feature (230) of actuator (216) within cavity (268). Longitudinal slot (262) is configured to receive central body portion (222). As shown in FIG. 12, lower body portion (220) includes lower rails (270). Actuator (216) may be rotated relative to slider (214) until actuator (216) contacts a stop feature (274) of upper body portion (218) and a stop feature (276) of lower body portion (220).

Unlike lower body portion (120) described above, lower body portion (220) includes outer engagement feature (265), which is shown a lower arcuate outer recess (272). However, it is also envisioned that outer engagement feature (265) may have a variety of suitable shapes and sizes. Lower arcuate outer recess (272) opens upwardly in an opposite direction than lower arcuate inner recess (266). Lower arcuate outer recess (272) includes a vertical interface surface (273a) and a horizontal interface surface (273b) that are shown as being perpendicular to each other.

4. Exemplary Central Body Portion

Central body portion (222) is similar to central body portion (122) and is described in greater detail below with reference to FIGS. 11-14. As shown in FIGS. 12 and 14, central body portion (222) includes an inner engagement feature (275) and an outer engagement feature (277). Inner engagement feature (275), shown as C-shaped engagement feature (278), engages upper and lower arcuate inner projections (232, 234) of inner engagement feature (230) of actuator (216). C-shaped engagement feature (278) includes upper and lower opposing retention features (280, 282) that are shown as being vertically oriented. C-shaped engagement feature (278) forms a cavity (284) that receives upper and lower arcuate inner projections (232, 234) of inner engagement feature (230) of actuator (216). Central body portion (222) includes lower rails (286). Lower rails (270) of lower body portion (220) and lower rails (286) of central body portion (222) are configured to slide along elongate channel (109), along proximal frame portion (18), to vertically guide slider (214) when moved distally. C-shaped engagement feature (288) collectively formed by upper and lower body portions (218, 220) is engaged with upper and lower arcuate inner projections (232, 234) of inner engagement feature (230) of actuator (216). As shown in FIGS. 11 and 13, C-shaped engagement feature (278) of central body portion (222) and C-shaped engagement feature (288) collectively formed by upper and lower body portions (218, 220) create cavities (268, 284) that are aligned to provide a track to prevent inner engagement feature (230) of actuator (216) from detaching.

Unlike central body portion (122) described above, central body portion (222) includes outer engagement feature (277). Outer engagement feature (277) of central body portion (122) includes upper and lower arcuate outer recesses (290, 292) that, together with upper and lower arcuate outer recesses (251, 272) of upper and lower body portions (118, 120), are configured to receive outer engagement feature (231) of actuator (216). Upper arcuate outer recess (290) includes a vertical interface surface (294a) and a horizontal interface surface (294b). Lower arcuate outer recess (292) includes a vertical interface surface (296a) and a horizontal interface surface (296b).

5. Exemplary Interface

Figure 15:
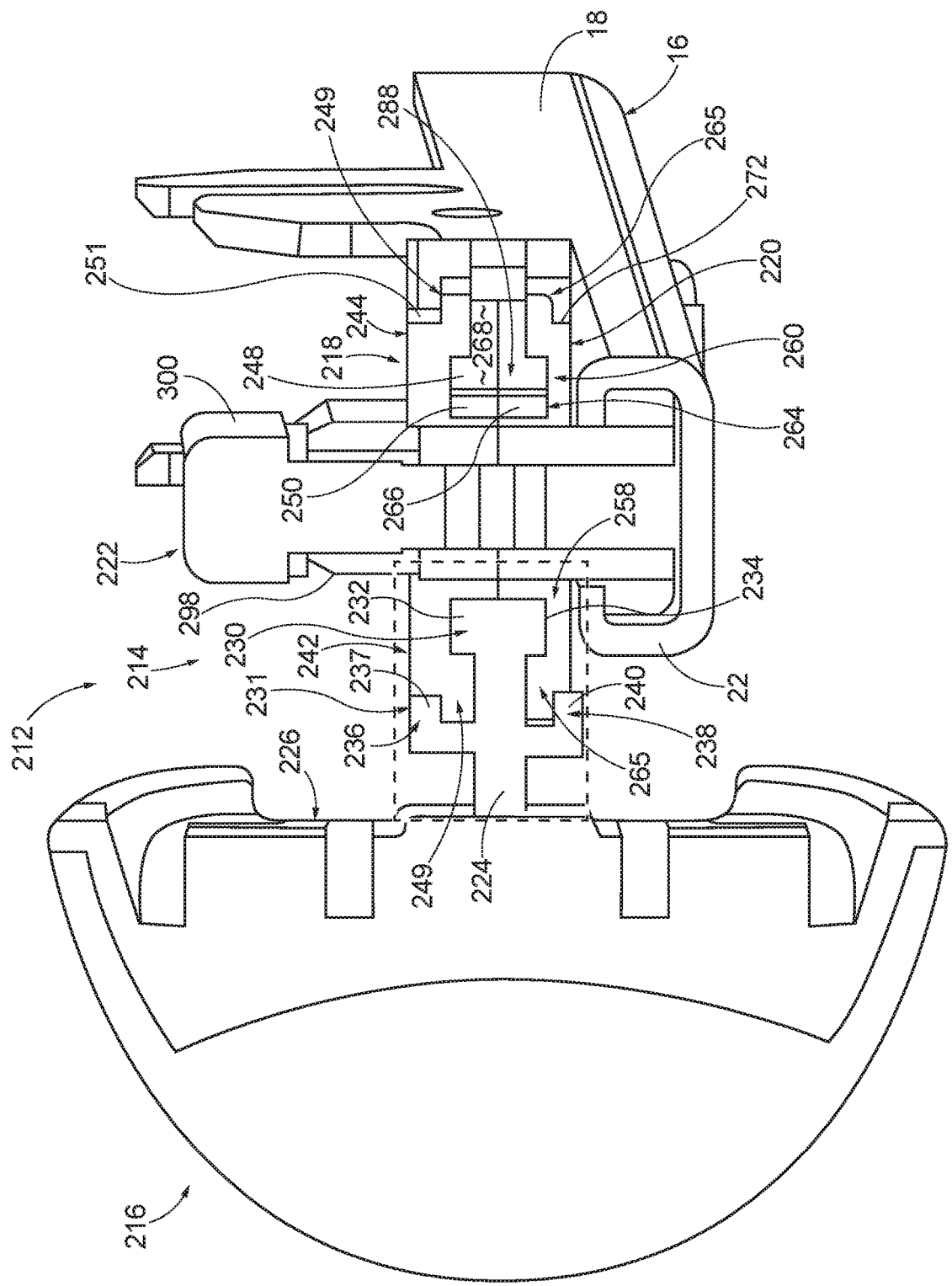
FIG. 15 depicts a cross-sectional perspective view of the firing assembly of FIG. 11 taken along from another view, where the inner engagement feature of the slider is engaged with the inner engagement feature of the actuator and the outer inner engagement feature of the slider is engaged with the outer engagement feature of the actuator.
Figure 17:
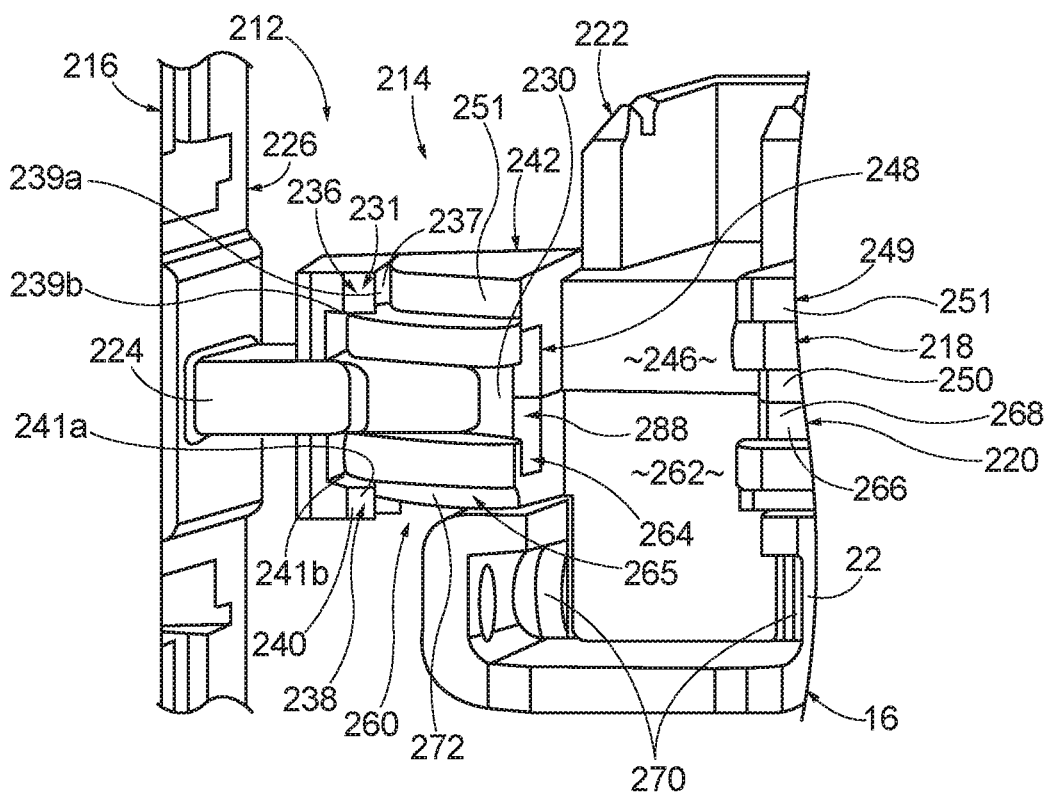
FIG. 17 depicts a perspective view of the firing assembly of FIG. 11 taken from another angle, where the inner engagement feature of the slider is engaged with the inner engagement feature of the actuator and the outer engagement feature of the slider is coupled with the outer engagement feature of the actuator.

With this structure in mind, FIGS. 15-17 show engagement of slider (214) and actuator (216) in greater detail. FIG. 15 shows a cross-sectional perspective view of firing assembly of FIG. 11 taken along from another view, where inner engagement feature (shown as inner engagement features (248, 264, 275)) of slider (214) is engaged at a first interface with an inner engagement feature (230) of actuator (216) and outer engagement feature (shown as outer engagement features (249, 265, 277)) of slider (214) is engaged at a second interface with outer engagement feature (231) of actuator (216). FIG. 16 shows an enlarged cross-sectional perspective view of an enlarged portion of FIG. 15. FIG. 17 shows a perspective view of firing assembly (212) of FIG. 11 taken along from another view, where inner engagement feature of slider (214) is engaged with an inner engagement feature (230) of actuator (216) and inner engagement feature of slider (214) is coupled with inner engagement feature (230) of actuator (216).

Inner engagement feature (230) of actuator (216) is configured to engage inner engagement feature (shown as inner engagement features (248, 264, 275)) of slider (214) at the first interface (e.g. an inner interface), when actuator (216) moves relative to slider (214). As shown, upper and lower arcuate inner projections (232, 234) of inner engagement feature (230) of actuator (216) are securably received within cavities (168, 184). Particularly, upper and lower arcuate inner projections (232, 234) are configured to slide along respective upper and lower arcuate recesses when actuator (216) moves relative to slider (214). Upper and lower arcuate outer recesses (251, 272) collectively extend a first lateral side (298) of slider (214) and a second lateral side (300) to guide upper and lower arcuate inner projections (232, 234) of actuator (216) between first and second lateral sides (298, 300) of slider (214).

Outer engagement feature (231) of actuator (216) is configured to engage outer engagement feature (shown as outer engagement features (249, 265, 277)) of slider (214) at the second interface (e.g. an outer interface), when actuator (216) moves relative to slider (214). For example, outer engagement feature (231) of actuator (216) may slide along outer engagement feature of slider (214), when actuator (216) moves between first and second lateral sides (298, 300) of slider (214).

Upper and lower L-shaped arcuate outer projections (236, 238) move relative to outer recesses of upper, lower, and central body portions (218, 220, 222). Upper and lower L-shaped arcuate outer projections (236, 238) are configured to be received in respective upper and lower outer arcuate recesses (251, 272) of upper and lower body portions (218, 220) and upper and lower outer arcuate recesses (290, 292) of central body portion (222) of slider (214). Particularly, upper L-shaped arcuate outer projection (236) is configured to slide along upper arcuate outer recesses (251, 290) when actuator (216) moves relative to slider (214), and lower L-shaped arcuate outer projection (238) is configured to slide along lower arcuate outer recesses (272, 292) when actuator (216) moves relative to slider (214).

Particularly, upper arcuate outer recesses (251, 290) and lower arcuate outer recesses (272, 292) extend from first lateral side (298) of slider (214) to second lateral side (300) of slider (214), such that upper arcuate outer recesses (251, 290) and lower arcuate outer recesses (272, 292) of upper, lower, and central body portions (218, 220, 222) collectively retain and guide upper and lower L-shaped arcuate outer projections (236, 238) of actuator (216) between first and second lateral sides (298, 300) of slider (214). Upper and lower tip portions (237, 240) are configured to be received in respective upper arcuate outer recesses (251, 290) and lower arcuate outer recesses (272, 292) of slider (214). Relative spacing between upper and lower arcuate inner projections (232, 234) of inner engagement feature (230) of actuator (216) are configured to securably receive and maintain inner engagement feature (230) of actuator (216) within cavities (268, 284).

Outer engagement features (shown as outer engagement features (249, 265, 277)) of slider (214) and actuator (216) provide at least one additional contact point to strengthen the second interface between slider (214) and actuator (216). As shown, the second interface is spaced from the first interface. Additional contact points are configured to limit deflection of actuator (216) relative to slider (214) to improve coupling of slider (214) and actuator (216). As shown in FIGS. 15-17, vertical interface surface (239a) of upper tip portion (237) of actuator (216) slides against vertical interface surface (253a) of upper body portion (218) and horizontal interface surface (239b) of upper tip portion (237) of actuator (216) slides against horizontal interface surface (253b) of upper body portion (218). Additionally, vertical interface surface (241a) of lower tip portion (240) of actuator (216) slides against vertical interface surface (273a) of lower body portion (220) and horizontal interface surface (241b) of upper tip portion (237) of actuator (216) slides against horizontal interface surface (273b) of lower body portion (220). Additionally, as shown in the exploded side view of FIG. 14, when actuator (216) is engaging central body portion (222), vertical interface surface (239a) of upper tip portion (237) of actuator (216) slides against vertical interface surface (294a) of central body portion (222) and horizontal interface surface (239b) of upper tip portion (237) of actuator (216) slides against horizontal interface surface (294b) of central body portion (222). Additionally, vertical interface surface (241a) of lower tip portion (240) of actuator (216) slides against vertical interface surface (296a) of central body portion (222) and horizontal interface surface (241b) of upper tip portion (237) of actuator (216) slides against horizontal interface surface (296b) of central body portion (222).

B. Exemplary Alternative Linear Surgical Stapler for Improved Actuator Support

Figure 18:
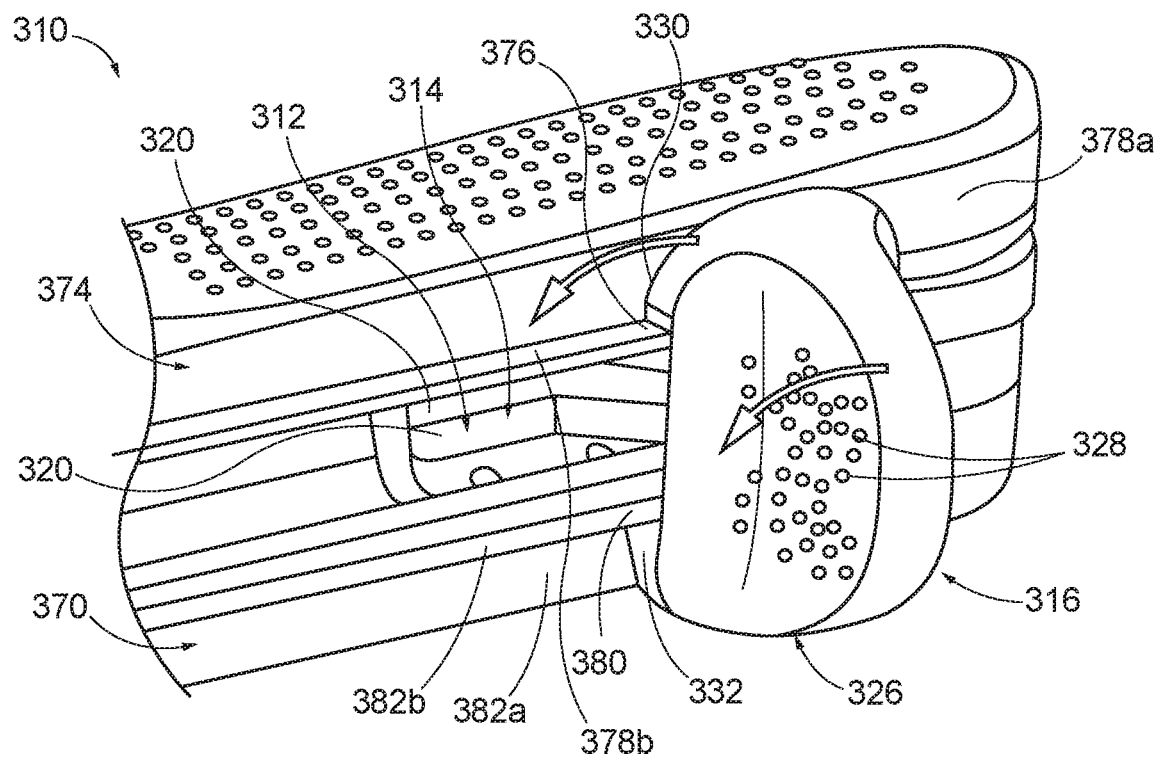
FIG. 18 depicts a proximal perspective view of an exemplary alternative linear surgical stapler, where upper and lower outer projections of an actuator are engaged with rails of the shrouds of the cartridge half and the anvil half.

FIG. 18 shows a proximal perspective view of another exemplary linear surgical stapler (310). Linear surgical stapler (310) is generally similar to linear surgical stapler (10) described above, except as where otherwise described below. Similar to linear surgical stapler (10), linear surgical stapler (310) includes a first elongate member (shown previously as anvil half (14)), a second elongate member (shown previously as cartridge half (12)), and a clamp member (shown previously as clamp lever (24)). As previously described with reference to linear surgical stapler (10), anvil half (14) includes a distal portion (shown previously as distal jaw portion (54)) that supports an anvil surface (shown as anvil plate (60)), where anvil plate (60) includes a plurality of staple forming pockets. Similar to firing assembly (34), firing assembly (312) is translatable from a first longitudinal position to a second longitudinal position to fire staple cartridge (80) when anvil half (14) is clamped against cartridge half (12). As previously described with reference to linear surgical stapler (10), cartridge half (12) includes a distal portion (shown as distal jaw portion (20)) configured to receive staple cartridge (80), and clamp lever (24) is operable to releasably clamp anvil half (14) against cartridge half (12).

As shown in FIG. 18, firing assembly (312) includes a slider (314) and an actuator (316). Slider (314) includes a first body portion (shown as upper body portion (318)) and a second body portion (shown as lower body portion (320)). Slider (314) may include a central body portion (not shown), but similar to central body portion (122). Actuator (316) includes a body (326) that may include gripping features (328) for improved gripping by a user. Actuator (316) is shown as including upper and lower projections (330, 332) that are configured to slidably engage shrouds (370, 374) of linear surgical stapler (310). As shown in FIG. 18, shroud (374) is similar to shroud (74), and includes an upper ledge (376). Upper ledge (376) includes a vertical interface surface (378a) and horizontal interface surface (378b). As shown, vertical interface surface (378a) is disposed at a 90-degree angle relative to horizontal interface surface (378b). Similarly, shroud (370), similar to shroud (70), includes a lower ledge (380) that is configured to engage lower projection (332) of actuator (316). Lower ledge (380) includes a vertical interface surface (382a) and horizontal interface surface (382b). Similarly, vertical interface surface (382a) is disposed at a 90-degree angle relative to horizontal interface surface (382b).

Figure 19:
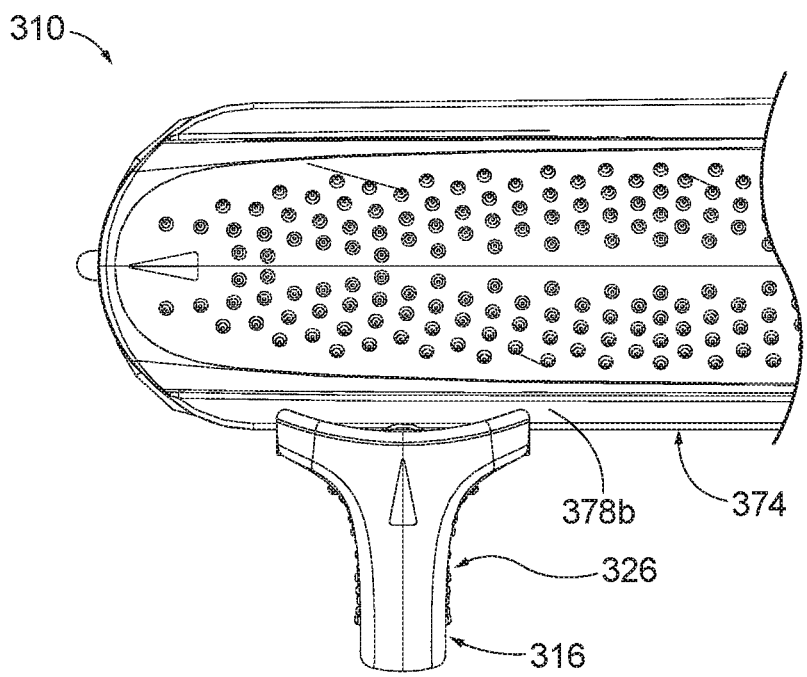
FIG. 19 depicts a top view of the upper projection of the actuator of FIG. 18 engaged with the rail of the shroud of the linear surgical stapler of FIG. 18.

Engagement of shrouds (370, 374) with actuator (316) may stabilize actuator (316) and control deflection and/or rotation of actuator (316) when a user applies force to actuator (316) when moved distally. FIG. 19 shows a top view of upper projection (330) of actuator (316) of FIG. 18 is engaged with upper ledge (376) of shroud (374) of linear surgical stapler (310) of FIG. 18. The interface between actuator (316) and shrouds (370, 374) brings actuator (316) to a 90-degree angle to shrouds (370, 374) and tightens the overhang for more engagement with upper and lower ledges (376, 380). The interface between actuator (316) and shrouds (370, 374) also may minimize separation of upper and lower body portions (318, 320) of slider (314).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a clamp member operable to releasably clamp the first elongate member against the second elongate member; and (d) a firing assembly, wherein the firing assembly is translatable from a first longitudinal position to a second longitudinal position to fire the staple cartridge when the first elongate member is clamped against the second elongate member, wherein the firing assembly comprises: (i) a slider that comprises: (A) an inner engagement feature, and (B) an outer engagement feature, and (ii) an actuator configured to be selectively actuated by a user, wherein the actuator comprises: (A) an inner engagement feature configured to engage with the inner engagement feature of the slider at a first interface when the actuator moves relative to the slider, and (B) an outer engagement feature configured to engage the outer engagement feature of the slider at a second interface when the actuator moves relative to the slider.

Example 2

The surgical stapler of Example 1, wherein the second interface is spaced from the first interface, wherein the first and second interfaces are configured to limit deflection of the actuator relative to the slider and to improve coupling of the slider and the actuator.

Example 3

The surgical stapler of any one or more of Examples 1 through 2, wherein the outer engagement feature of the slider is formed in an outer surface of the slider, wherein the outer engagement feature of the actuator is configured to slide along the outer engagement feature of the slider when the actuator moves between a first lateral side of the slider and a second lateral side of the slider.

Example 4

The surgical stapler of any one or more of Examples 1 through 2, wherein the outer engagement feature of the slider includes a first outer recess, wherein the outer engagement feature of the actuator includes a first outer projection, wherein the first outer projection is configured to slide along the first outer recess when the actuator moves between a first lateral side of the slider and a second lateral side of the slider.

Example 5

The surgical stapler of Example 4, wherein the outer engagement feature of the slider includes a second outer recess, wherein the outer engagement feature of the actuator includes a second outer projection, wherein the second outer projection is configured to slide along the second outer recess when the actuator moves relative to the slider.

Example 6

The surgical stapler of Example 5, wherein the first and second outer projections of the actuator include upper and lower arcuate outer projections, wherein the first and second outer recesses of the slider include upper and lower arcuate outer recesses, wherein the upper and lower arcuate outer projections are configured to slide along the upper and lower arcuate outer recesses respectively when the actuator moves relative to the slider.

Example 7

The surgical stapler of Example 5, wherein the actuator includes an arm that extends perpendicular to the actuator, wherein the first and second outer projections include first and second L-shaped outer projections that extend from the arm, wherein the first and second L-shaped outer projections are configured to be received in the respective first and second outer recesses of the slider.

Example 8

The surgical stapler of Example 7, wherein the first and second L-shaped projections include first and second tip portions, wherein the first and second tip portions of the first and second L-shaped outer projections extend parallel to the arm of the outer engagement feature of the actuator and are configured to be received in the respective first and second outer recesses of the slider.

Example 9

The surgical stapler of any one or more of Examples 7 through 8, wherein the inner engagement feature of the actuator includes first and second inner projections that extend opposite one another and perpendicular to the arm of the outer engagement feature of the actuator.

Example 10

The surgical stapler of Example 9, wherein the first and second L-shaped outer projections and the first and second inner projections are arcuate.

Example 11

The surgical stapler of any one or more of Examples 1 through 10, wherein the inner engagement feature of the slider includes a C-shaped engagement feature, wherein the C-shaped engagement feature forms a cavity configured to receive the inner engagement feature of the actuator.

Example 12

The surgical stapler of any one or more of Examples 1 through 11, wherein the inner engagement feature of the actuator includes first and second opposing inner projections that extend opposite one another, wherein the first and second inner projections are configured to be securably received within the cavity.

Example 13

The surgical stapler of any one or more of Examples 1 through 3, wherein the slider includes first and second body portions that each include first and second outer recesses, wherein the outer engagement feature of the slider includes the first and second outer recesses that are configured to receive the outer engagement feature of the actuator.

Example 14

The surgical stapler of Example 13, wherein the slider includes a third body portion that includes inner and outer engagement features, wherein the outer engagement feature of the third body portion includes first and second outer recesses that, together with the first and second outer recesses of the first and second body portions, are configured to receive the outer engagement feature of the actuator.

Example 15

The surgical stapler of Example 14, wherein the first and second outer recesses of the first, second, and third body portions collectively extend along a first lateral side of the slider and a second lateral side to guide the outer engagement feature of the actuator between the first and second lateral sides of the slider.

Example 16

A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a clamp member operable to releasably clamp the first elongate member against the second elongate member; and (d) a firing assembly, wherein the firing assembly is translatable from a first longitudinal position to a second longitudinal position to fire the staple cartridge when the first elongate member is clamped against the second elongate member, wherein the firing assembly comprises: (i) a slider that includes first and second outer recesses that open in opposite directions, and (ii) an actuator configured to be selectively actuated by a user, wherein the actuator comprises: (A) a body, (B) a first outer projection extending from the body, wherein the first outer projection is configured to slide along the first outer recess when the actuator moves relative to the slider, and (C) a second outer projection extending from body, wherein the second outer projection is configured to slide along the second outer recess when the actuator moves relative to the slider.

Example 17

The surgical stapler of Example 16, wherein the first and second outer projections include first and second L-shaped outer projections that are configured to be received in the first and second outer recesses of the slider, wherein tips of the first and second L-shaped outer projections extend parallel to the body.

Example 18

A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a clamp member operable to releasably clamp the first elongate member against the second elongate member; and (d) a firing assembly, wherein the firing assembly is translatable from a first longitudinal position to a second longitudinal position to fire the staple cartridge when the first elongate member is clamped against the second elongate member, wherein the firing assembly comprises: (i) a slider comprising: (A) a first body portion that includes an inner engagement feature and an outer engagement feature, (B) a second body portion that includes an inner engagement feature and an outer engagement feature, and (C) a third body portion that includes an inner engagement feature and an outer engagement feature, and (ii) an actuator comprising: (A) an inner engagement feature configured to move relative the inner engagement features of the first, second, and third body portions, and (B) an outer engagement feature configured to move relative to the outer engagement features of the first, second, and third body portions.

Example 19

The surgical stapler of Example 18, wherein the outer engagement features of the first, second, and third body portions respectively include first, second, and third outer recesses, wherein the first, second, and third outer recesses collectively extend from a first lateral side of the slider and a second lateral side of the slider such that the first, second, and third outer recesses of the first, second, and third body portions collectively retain and guide the outer engagement feature of the actuator between the first and second lateral sides of the slider.

Example 20

The surgical stapler of any one or more of Example 18 through 19, wherein the inner engagement features of the first, second, and third body portions respectively include first, second, and third inner recesses that collectively form a cavity, wherein the inner engagement feature of the actuator includes first and second inner projections configured to be securably received within the cavity.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed on Feb. 6, 2018, issued as U.S. Pat. No. 10,631,866 on Apr. 28, 2020; U.S. application Ser. No. 15/889,370, entitled "Lockout Assembly for Linear Surgical Stapler," filed on Feb. 6, 2018, issued as U.S. Pat. No. 10,667,818 on Jun. 2, 2020; U.S. application Ser. No. 15/889,374, entitled "Features to Align and Close Linear Surgical Stapler"," filed on Feb. 6, 2018, issued as U.S. Pat. No. 10,932,781 on Mar. 2, 2021; U.S. application Ser. No. 15/889,376, entitled "Releasable Engagement features for Proximal Portions of Linear Surgical Stapler," filed on Feb. 6, 2018, issued as U.S. Pat. No. 10,898,197 on Jan. 26, 2021; U.S. application Ser. No. 15/889,388, entitled "Firing Lever Assembly for Linear Surgical Stapler," filed on Feb. 6, 2018, issued as U.S. Pat. No. 10,874,398 on Dec. 29, 2020; U.S. application Ser. No. 15/889,390, entitled "Clamping Mechanism for Linear Surgical Stapler," filed on Feb. 6, 2018, issued as U.S. Pat. No. 10,687,819 on Jun. 23, 2020; and/or U.S. application Ser. No. 16/410,006, entitled "Actuator Retainer for Surgical Stapler," filed on May 13, 2019, published as U.S. Pub. No. 2020/0360015 on Nov. 19, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
   (a) a first elongate member having a distal portion that supports an anvil surface, wherein the anvil surface includes a plurality of staple forming pockets;
   (b) a second elongate member having a distal portion configured to receive a staple cartridge;
   (c) a clamp member operable to releasably clamp the first elongate member against the second elongate member; and
   (d) a firing assembly, wherein the firing assembly is translatable from a first longitudinal position to a second longitudinal position to fire the staple cartridge when the first elongate member is clamped against the second elongate member, wherein the firing assembly comprises:
      (i) a slider that comprises:
         (A) an inner engagement feature, and
         (B) an outer engagement feature, and
      (ii) an actuator comprising:
         (A) a body configured to be selectively actuated by a user,
         (B) an inner engagement feature configured to engage with the inner engagement feature of the slider when the actuator moves relative to the slider, and
         (C) an outer engagement feature having a tip portion that extends in a direction away from the body of the actuator, wherein the tip portion is configured to engage the outer engagement feature of the slider when the actuator moves relative to the slider.

2. The surgical stapler of claim 1, wherein the outer engagement features are spaced from the inner engagement features, wherein the inner and outer engagement features of the slider and the actuator are configured to limit deflection of the actuator relative to the slider and to improve coupling of the slider and the actuator.

3. The surgical stapler of claim 2, wherein the outer engagement feature of the slider includes a first outer recess, wherein the outer engagement feature of the actuator includes a first outer projection, wherein the first outer projection has the tip portion, wherein the first outer projection is configured to slide along the first outer recess when the actuator moves between a first lateral side of the slider and a second lateral side of the slider.

4. The surgical stapler of claim 3, wherein the outer engagement feature of the slider includes a second outer recess, wherein the outer engagement feature of the actuator includes a second outer projection, wherein the second outer projection is configured to slide along the second outer recess when the actuator moves relative to the slider.

5. The surgical stapler of claim 4, wherein the first and second outer projections of the actuator include upper and lower arcuate outer projections, wherein the first and second outer recesses of the slider include upper and lower arcuate outer recesses, wherein the upper and lower arcuate outer projections are configured to slide along the upper and lower arcuate outer recesses respectively when the actuator moves relative to the slider.

6. The surgical stapler of claim 4, wherein the actuator includes an arm that extends perpendicular to the body of the actuator, wherein the first and second outer projections include first and second L-shaped outer projections that extend from the arm, wherein the first and second L-shaped outer projections are configured to be received in the respective first and second outer recesses of the slider.

7. The surgical stapler of claim 6, wherein the first L-shaped outer projection includes the tip portion, wherein the second L-shaped outer projection includes a tip portion, wherein the first and second tip portions of the first and second L-shaped outer projections extend parallel to the arm of the outer engagement feature of the actuator and are configured to be received in the respective first and second outer recesses of the slider.

8. The surgical stapler of claim 6, wherein the inner engagement feature of the actuator includes first and second inner projections that extend opposite one another and perpendicular to the arm of the outer engagement feature of the actuator.

9. The surgical stapler of claim 1, wherein the outer engagement feature of the slider is formed in an outer surface of the slider, wherein the outer engagement feature of the actuator is configured to slide along the outer engagement feature of the slider when the actuator moves between a first lateral side of the slider and a second lateral side of the slider.

10. The surgical stapler of claim 1, wherein the inner engagement feature of the slider includes a C-shaped engagement feature, wherein the C-shaped engagement feature forms a cavity configured to receive the inner engagement feature of the actuator.

11. The surgical stapler of claim 10, wherein the inner engagement feature of the actuator includes first and second opposing inner projections that extend opposite one another, wherein the first and second inner projections are configured to be securably received within the cavity.

12. The surgical stapler of claim 1, wherein the slider includes first and second body portions that each include first and second outer recesses, wherein the outer engagement feature of the slider includes the first and second outer recesses that are configured to receive the outer engagement feature of the actuator.

13. The surgical stapler of claim 12, wherein the slider includes a third body portion that includes inner and outer engagement features, wherein the outer engagement feature of the third body portion includes first and second outer recesses that, together with the first and second outer recesses of the first and second body portions, are configured to receive the outer engagement feature of the actuator.

14. The surgical stapler of claim 13, wherein the first and second outer recesses of the first, second, and third body portions collectively extend along a first lateral side of the slider and a second lateral side to guide the outer engagement feature of the actuator between the first and second lateral sides of the slider.

15. A surgical stapler comprising:
(a) a first elongate member having a distal portion that supports an anvil surface, wherein the anvil surface includes a plurality of staple forming pockets;
(b) a second elongate member having a distal portion configured to receive a staple cartridge;
(c) a clamp member operable to releasably clamp the first elongate member against the second elongate member; and
(d) a firing assembly, wherein the firing assembly is translatable from a first longitudinal position to a second longitudinal position to fire the staple cartridge when the first elongate member is clamped against the second elongate member, wherein the firing assembly comprises:
    (i) a slider that includes first and second outer recesses that open in opposite directions, and
    (ii) an actuator configured to be selectively actuated by a user, wherein the actuator comprises:
        (A) a body, and
        (B) a first outer projection having a tip portion extending in a direction away from the body, wherein the first outer projection is configured to slide along the first outer recess when the actuator moves relative to the slider.

16. The surgical stapler of claim 15, wherein the actuator further comprises a second outer projection extending from body, wherein the second outer projection is configured to slide along the second outer recess when the actuator moves relative to the slider.

17. The surgical stapler of claim 16, wherein the first and second outer projections include first and second L-shaped outer projections that are configured to be received in the first and second outer recesses of the slider, wherein the second outer projection has a tip portion extending in a direction away from body, wherein the tip portions of the first and second L-shaped outer projections extend parallel to the body.

18. A surgical stapler comprising:
(a) a first elongate member having a distal portion that supports an anvil surface, wherein the anvil surface includes a plurality of staple forming pockets;
(b) a second elongate member having a distal portion configured to receive a staple cartridge;
(c) a clamp member operable to releasably clamp the first elongate member against the second elongate member; and
(d) a firing assembly, wherein the firing assembly is translatable from a first longitudinal position to a second longitudinal position to fire the staple cartridge when the first elongate member is clamped against the second elongate member, wherein the firing assembly comprises:
    (i) a slider comprising:
        (A) a first body portion that includes an engagement feature,
        (B) a second body portion that includes an engagement feature, and
        (C) a third body portion that includes an engagement feature, and
    (ii) an actuator comprising:
        (A) a body, and
        (B) an engagement feature having a tip portion that extends in a direction away from the body of the actuator, wherein the tip portion is configured to engage the engagement features of the slider when the actuator moves relative to the slider.

19. The surgical stapler of claim 18, wherein the first, second, and third body portions respectively include first, second, and third recesses, wherein the first, second, and third recesses collectively extend from a first lateral side of the slider and a second lateral side of the slider such that the first, second, and third recesses of the first, second, and third body portions collectively retain and guide the engagement feature of the actuator between the first and second lateral sides of the slider.

20. The surgical stapler of claim 19, wherein the first, second, and third body portions further include first, second, and third recesses that collectively form a cavity, wherein the actuator further includes first and second projections configured to be securably received within the cavity.

* * * * *